(12) United States Patent
Baden et al.

(10) Patent No.: US 6,291,744 B1
(45) Date of Patent: Sep. 18, 2001

(54) NUCLEIC ACIDS ENCODING PLANT GROUP 2 PROTEINS AND USES THEREOF

(75) Inventors: Catherine S. Baden, Martinez; Pamela Dunsmuir, Piedmont; Kathleen Y. Lee, Oakland, all of CA (US)

(73) Assignee: DNA Plant Technology Corporation, Oakland, CA (US)

( * ) Notice: Subject to any disclaimer, the term of this patent is extended or adjusted under 35 U.S.C. 154(b) by 0 days.

(21) Appl. No.: 09/127,646

(22) Filed: Jul. 31, 1998

Related U.S. Application Data

(63) Continuation-in-part of application No. 08/761,549, filed on Dec. 6, 1996, now Pat. No. 5,981,727, which is a continuation-in-part of application No. 08/289,458, filed on Aug. 20, 1994, now Pat. No. 5,608,144.

(51) Int. Cl.$^7$ .............................. A01H 5/00; C12N 15/82
(52) U.S. Cl. ..................... 800/301; 800/278; 800/279; 800/287; 536/23.6; 435/320.1; 435/419; 435/468
(58) Field of Search .................... 536/23.6; 800/278, 800/279, 298, 301, 287; 435/69.1, 320.1, 419, 468

(56) References Cited

U.S. PATENT DOCUMENTS

| | | | |
|---|---|---|---|
| 4,495,280 | 1/1985 | Bujard | 435/6 |
| 4,518,690 | 5/1985 | Guntaka | 435/71 |
| 4,551,433 | 11/1985 | DeBoer | 435/253 |
| 5,110,732 | * 5/1992 | Benfey et al. | 435/172.3 |
| 5,187,267 | 2/1993 | Comai | 536/23.1 |

FOREIGN PATENT DOCUMENTS

| | | |
|---|---|---|
| 0 409 625 A1 | 1/1991 | (EP) . |
| WO/93/07257 | 4/1993 | (WO) . |

OTHER PUBLICATIONS

Oommen et al (1994) The Plant Cell 6: 1789–1803.*
Van Haaren et al (1991) Plant Mol. Biol. 17: 615–630.*
Pear et al (1989) Plant Mol. Biol. 13: 639–651.*
Lewin (1985) In: *Genes*, 2$^{nd}$ ed., pp 182–183, John Wiley & Sons, NY.*
Herrera–Estrella, Luis, et al. (1983) "Expression of chimaeric genes transferred into plant cells using a Ti–plasmid–derived vector", *Nature* 303:209–213.
DellaPenna, Dean, et al. (1986) "Molecular cloning of tomato fruit polygalacturonase: Analysis of polygalacturonase mRNA levels during ripening", *Proc. Natl. Acad. Sci USA*, 83:6420–6424.

Deikman, Jill, et al. (1988) "Interaction of a DNA binding factor with 5'–flanking region of an ethylene–responsive fruit ripening gene from tomato", *The EMBO Journal*, 7(11):3315–3320.
Cordes, Sabine, et al. (1989) "Interaction of a Developmentally Regulated DNA–Binding Factor with Sites Flanking Two Different Fruit–Ripening Genes from Tomato", *The Plant Cell*, 1:1025–1034.
Shirsat, Anil, et al. (1989) "Sequences responsible for the tissue specific promoter activity of a pea legumin gene in tobacco", *Mol Gen Genet*, 215:326–331.
Kuhlemeier, Cris, et al. (1989) "The Pea rbcS–3A Promoter Mediates Light Responsiveness but not Organ Specificity", *The Plant Cell*, 1:471–478.
Gidoni, David, et al. (1988) "Coordinated expression between two photosynthetic petunia genes in transgenic plants", *Mol Gen Genet*, 211:507–514.
Kononowicz, Halina, et al. (1992) "Subdomains of the Octopine Synthase Upstream Activating Element Direct Cell–Specific Expression in Transgenic Tobacco Plants", *The Plant Cell*, 4:17–27.
An, Gynhueng, et al. (1990) "Nopaline Synthase Promoter is Wound Inducible and Auxin Inducible", *The Plant Cell*, 2:225–233.
Benfey, Philip N., et al. (1990) "The Cauliflower Mosaic Virus 35S Promoter: Combinatorial Regulation of Transcription in Plants", *Science*, 250:959–966.
Odell, Joan T., et al. (1985) "Identification of DNA Sequences required for activity of the cauliflower mosaic virus 35S promoter", *Nature*, 313:810–812.
Hammond, Rosemarie W., et al. (1984) "Molecular Cloning and Analysis of a Gene Coding for the Bowman–Birk Protease Inhibitor in Soybean", *The Journal of Biological Chemistry*, 249(15):9883–9890.

* cited by examiner

Primary Examiner—Elizabeth F. McElwain
(74) Attorney, Agent, or Firm—Townsend and Townsend and Crew LLP

(57) ABSTRACT

This invention relates to compositions and methods useful in the production of transgenic plants. In particular, the invention relates to nucleic acids that hybridizes under stringent conditions to a nucleic acid encoding a plant Gp2 protein that has the amino acid sequence depicted in SEQ ID NO:1 or SEQ ID NO:2. The invention also relates to the above-described nucleic acid operably linked to a heterologous or Gp2 plant promoter. In addition, the invention relates to transgenic plants containing the above-described nucleic acids.

27 Claims, 8 Drawing Sheets

PEP 4-2

PEP4-6

PEP4-6ACCS

SEQUENCE LISTING

<160> NUMBER OF SEQ ID NOS: 12

<210> SEQ ID NO 1
<211> LENGTH: 594
<212> TYPE: DNA
<213> ORGANISM: Capsicum annuum
<220> FEATURE:
<221> NAME/KEY: CDS
<222> LOCATION: (46)..(273)
<223> OTHER INFORMATION: pepper plant Group 2 (Gp2) protein cDNA

<400> SEQUENCE: 1

```
gaaattatta tttgaaaaaa aaaaaaaga tccaaaaata ttatt atg gct ggc ttt      57
                                                Met Ala Gly Phe
                                                  1 tcc aaa gta gtt gca act att ttt ctt atg atg ttg ctg gtt ttt gct    105
Ser Lys Val Val Ala Thr Ile Phe Leu Met Met Leu Leu Val Phe Ala
  5                  10                  15                  20 act gat atg atg gcg gag gca aag atc tgc gag gcg ttg acg ggc aac    153
Thr Asp Met Met Ala Glu Ala Lys Ile Cys Glu Ala Leu Thr Gly Asn
                 25                  30                  35 ttc aag ggg ttg tgc ctt agt agc cgc gat tgt ggt aat gtt tgc cgt    201
Phe Lys Gly Leu Cys Leu Ser Ser Arg Asp Cys Gly Asn Val Cys Arg
             40                  45                  50 aga gag gga ttt acc gat ggc tct tgc att gga ttc cgt ctt caa tgc    249
Arg Glu Gly Phe Thr Asp Gly Ser Cys Ile Gly Phe Arg Leu Gln Cys
         55                  60                  65 ttc tgc acg aag ccc tgt gct taattaactc ttgagaggtg aaagtctga        300
Phe Cys Thr Lys Pro Cys Ala
     70                  75 tggatagatt gaaaaaagat aaattactat gaattaatga gtattttata gtttgttgtt  360
gtgcttttat ttgtcatgaa ataaagacca tttggattaa tggttgctat ggaaaaaaag  420
ctgttgtcaa cttttgattg taagtttttt gtttggaagg ttgttatcta aagtattgta  480
tcgtgttgtt agtttaaata tttatgttga ttgttagttg aattttatat tgtattgtgt  540
```

```
ctgtaaatta tattattatg tcacgattaa aagtcttatt ttgatgtgat gatc         594
```

<210> SEQ ID NO 2
<211> LENGTH: 75
<212> TYPE: PRT
<213> ORGANISM: Capsicum annuum

<400> SEQUENCE: 2

```
Met Ala Gly Phe Ser Lys Val Val Ala Thr Ile Phe Leu Met Met Leu
 1               5                  10                  15

Leu Val Phe Ala Thr Asp Met Met Ala Glu Ala Lys Ile Cys Glu Ala
            20                  25                  30

Leu Thr Gly Asn Phe Lys Gly Leu Cys Leu Ser Ser Arg Asp Cys Gly
        35                  40                  45

Asn Val Cys Arg Arg Glu Gly Phe Thr Asp Gly Ser Cys Ile Gly Phe
    50                  55                  60

Arg Leu Gln Cys Phe Cys Thr Lys Pro Cys Ala
65                  70                  75
```

<210> SEQ ID NO 3
<211> LENGTH: 1727
<212> TYPE: DNA
<213> ORGANISM: Capsicum annuum
<220> FEATURE:
<221> NAME/KEY: misc_feature
<222> LOCATION: (1)..(1727)
<223> OTHER INFORMATION: pepper plant Group 2 (Gp2) genomic DNA clone
<220> FEATURE:
<221> NAME/KEY: promoter
<222> LOCATION: (1)..(1233)
<223> OTHER INFORMATION: Gp2 promoter sequence
<220> FEATURE:
<221> NAME/KEY: CAAT_signal
<222> LOCATION: (1100)..(1103)
<220> FEATURE:
<221> NAME/KEY: TATA_signal
<222> LOCATION: (1139)..(1146)
<220> FEATURE:
<221> NAME/KEY: misc_feature
<222> LOCATION: (1169)
<223> OTHER INFORMATION: transcriptional start site
<220> FEATURE:
<221> NAME/KEY: misc_feature
<222> LOCATION: (1172)
<223> OTHER INFORMATION: pGP50 5' end
<220> FEATURE:
<221> NAME/KEY: misc_feature
<222> LOCATION: (1234)..(1236)
<223> OTHER INFORMATION: translation start codon
<220> FEATURE:
<221> NAME/KEY: intron
<222> LOCATION: (1298)
<223> OTHER INFORMATION: intron start site

<400> SEQUENCE: 3

```
ttttaactgt gattttacta tatcgtccct aattaatcat tataggacat ttatgtatta    60
aaaagtcaat aatatttaat taaaaataga ttactataat acccccctatc attactatat   120 taccccctaat tgctccgtga tttactatat tatcccctaat taattattat aagccattat  180
atattataat taataatata tttattatat tatctctaat taattattat aagtcattta    240
tatattagaa ttaataatat ttaattaaaa tagatgtcat gtctgcctat attacccccta  300 attgctccat aatttactgt attacccccta attaattgtt ataagtcatt tatatattag   360
aattagtaat attttttaata ctatattacc cctaattaat tattataagt catttggttt   420
cgatcgctgc ttcatcattt actatttacc cctaatttct ccatgattta ctctattacc   480
```

-continued

```
ccttattaat tattataagt cattgatata ttagaattaa taatatattt ttattatatt        540
acccctaatt aattattata agtcatttat atattagaat taataatatt taattaaaaa        600
aatagatatt tatgacgttt gtttcagcta ctttaaccgt gattttacta tatcatcctt        660
aattaattat tataagtcat ttatttatta aaaattaat aatatataat taaaaaatag         720
atgacatgtc tgcctatatt acccctaatt aattattata agtcatttat ttattaaaaa        780
attaataata tataattaaa aaattgatga gacatacttg aactttagga gggtcatatt        840
acccctagat taattaaaat cgtattttg acaaccttag tgcctacgtg gaccttcagt         900
gtgttgattt actgacgtac cactgttggg agcactacct ccataatggg ccctacaacg        960
cgcgattcag attagttgag actccaatac ggacatcaaa aatagatgga aaaccgaaaa       1020
aaaacaaaat aaaaataatg tgtgtttaat tttcatttgt agattagtca aagttataca       1080
ctcacaaatt catgataatc aacttttca tcatacatgg ctaggctttt tgaaaatcta        1140
tatatattta gtagtggcgt cttcattctt tacccacata gaagaaatag aaattattat       1200
ttgaaaaaaa aaaaagatc caaaatatt attatggctg gcttttccaa gtagttgca          1260 actatttttc ttatgatgtt gctggttttt gctactggta attcattttc ttttctttt        1320 ttccaaagta gttcaactaa tggtatgacg atatttaata caacaacata tcaagtacta       1380
aaatttcaca agtgaggtct gaaaaaggta aagtgtatac agaatatata tataaaaact      1440
atttcttcac tcgtttgaac tcttatgtta aatttaaagg cggattctgc aagttcaact      1500
aatggtatga cggtatttaa tacaacaata atatgtcagt agtaaatttt cacgagtgag      1560
gtctgagaaa ggtaaagtgt acataggttt aattttacca ttacttcgga gcagtggcgg      1620
aaccagaaat ttgatgaaga tagtgtaaat tgcagttgct tcaagggtgt gcaaaattaa      1680
atatatactc ataatagcca acatttaacc tatatacaca ataccag                   1727
```

<210> SEQ ID NO 4
<211> LENGTH: 1233
<212> TYPE: DNA
<213> ORGANISM: Capsicum annuum
<220> FEATURE:
<221> NAME/KEY: promoter
<222> LOCATION: (1)..(1233)
<223> OTHER INFORMATION: pepper plant Group 2 (Gp2) promoter sequence
      up to the ATG start codon
<220> FEATURE:
<221> NAME/KEY: CAAT_signal
<222> LOCATION: (1100)..(1103)
<220> FEATURE:
<221> NAME/KEY: TATA_signal
<222> LOCATION: (1139)..(1146)
<220> FEATURE:
<221> NAME/KEY: misc_feature
<222> LOCATION: (1169)
<223> OTHER INFORMATION: transcriptional start site
<220> FEATURE:
<221> NAME/KEY: misc_feature
<222> LOCATION: (1172)
<223> OTHER INFORMATION: pGP50 5' end

<400> SEQUENCE: 4

```
ttttaactgt gattttacta tatcgtccct aattaatcat tataggacat ttatgtatta         60
aaaagtcaat aatattttaat taaaatataga ttactataat accccctatc attactatat       120 taccccctaat tgctccgtga tttactatat tatccctaat taattattat aagccattat        180
atattataat taataaatata tttattatat tatctctaat taattattat aagtcattta        240
tatattagaa ttaataatat ttaattaaaaa tagatgtcat gtctgcctat attaccccta        300
```

-continued

```
attgctccat aatttactgt attacccta attaattgtt ataagtcatt tatatattag    360
aattagtaat attttaata ctatattacc cctaattaat tattataagt catttggttt    420
cgatcgctgc ttcatcattt actatttacc cctaatttct ccatgattta ctctattacc    480
ccttattaat tattataagt cattgatata ttagaattaa taatatattt ttattatatt    540
acccctaatt aattattata agtcatttat atattagaat taataatatt taattaaaaa    600
aatagatatt tatgacgttt gtttcagcta ctttaaccgt gattttacta tatcatcctt    660
aattaattat tataagtcat ttatttatta aaaaattaat aatatataat taaaaaatag    720
atgacatgtc tgcctatatt acccctaatt aattattata agtcatttat ttattaaaaa    780
attaataata tataattaaa aaattgatga gacatacttg aactttagga gggtcatatt    840
acccctagat taattaaaat cgtattttg acaaccttag tgcctacgtg gaccttcagt    900
gtgttgattt actgacgtac cactgttggg agcactacct ccataatggg ccctacaacg    960
cgcgattcag attagttgag actccaatac ggacatcaaa aatagatgga aaaccgaaaa    1020
aaaacaaaat aaaaataatg tgtgtttaat tttcatttgt agattagtca aagttataca    1080
ctcacaaatt catgataatc aacttttca tcatacatgg ctaggctttt tgaaaatcta    1140
tatatattta gtagtggcgt cttcattctt tacccacata gaagaaatag aaattattat    1200
ttgaaaaaaa aaaaaagatc caaaaatatt att                                1233
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide beginning 19 bp downstream of translation start
      for primer extension analysis

<400> SEQUENCE: 5
ctactttgga aaagccagcc                                                 20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      oligonucleotide sequence surrounding translation start to
      introduce a NcoI restriction site by site directed mutagenesis

<400> SEQUENCE: 6
gccagccatg gtaatatttt tgg                                             23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer
      oligonucleotide 13 bp downstream of translation
      start in uidA gene

<400> SEQUENCE: 7
gatttcacgg gttggggttt                                                 20

<210> SEQ ID NO 8
<211> LENGTH: 20
<212> TYPE: DNA
<213> ORGANISM: Artificial Sequence

```
<220> FEATURE:
<223> OTHER INFORMATION: Description of Artificial Sequence:
      oligonucleotide introducing XbaI site 17 bpdownstream of GP2 stop
      codon by site directed mutagenesis

<400> SEQUENCE: 8
gaaagtctag atggatatag                                               20

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:degenerate
      oligonucleotide Oligo #1
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (21)
<223> OTHER INFORMATION: i
<220> FEATURE:
<221> NAME/KEY: modified_base
<222> LOCATION: (24)
<223> OTHER INFORMATION: i

<400> SEQUENCE: 9
ttrtcnccng crtcrtarta nccncc                                        26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:degenerate
      oligonucleotide Oligo#2
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i

<400> SEQUENCE: 10
tccatrtcyt cnggncgytc ccarca                                        26

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      oligonucleotide Oligo #3 introducing NcoI site at the translation
      start by site directed mutagenesis

<400> SEQUENCE: 11
atatatataa ccatggcttg                                               20

<210> SEQ ID NO 12
<211> LENGTH: 19
<212> TYPE: DNA
<213> ORGANISM: Artificial Sequence
<220> FEATURE:
```

-continued

```
<223> OTHER INFORMATION: Description of Artificial Sequence:
      oligonucleotide Oligo #4 introducing BglII site adjacent to
      translation stop

<400> SEQUENCE: 12
aaattgaaga tctatagtc                                                  19
```

NUCLEIC ACIDS ENCODING PLANT GROUP 2 PROTEINS AND USES THEREOF

CROSS-REFERENCE TO RELATED APPLICATIONS

This application is a continuation-in-part of application U.S. Ser. No. 08/761,549, filed Dec. 6, 1996 now U.S. Pat. No. 5,981,727, which is a continuation-in-part of application U.S. Ser. No. 08/289,458, filed Aug. 20, 1994 (now U.S. Pat. No. 5,608,144). This application claims the benefit of both application U.S. Ser. No. 08/761,549 and U.S. Pat. No. 5,608,144, the contents of which are incorporated herein by reference.

STATEMENT REGARDING FEDERALLY SPONSORED RESEARCH OR DEVELOPMENT

Not Applicable.

BACKGROUND OF THE INVENTION

This invention relates to compositions and methods useful in the production of transgenic plants. In particular, the invention relates to a nucleic acid that hybridizes under stringent conditions to a nucleic acid encoding a plant Group 2 ("Gp2") protein that has the amino acid sequence depicted in SEQ ID NO:1 or SEQ ID NO:2. The invention also relates to the above-described nucleic acid operably linked to a heterologous promoter. In addition, the invention relates to transgenic plants containing the above-described nucleic acid.

The invention also relates to Gp2 plant promoter sequences and to expression cassettes containing Gp2 plant promoter sequences. The invention also relates to vectors and transgenic plants containing Gp2 plant promoter sequences that are operably linked to heterologous DNA sequences. In addition, the invention relates to methods of producing transgenic plants by using vectors containing Gp2 promoter sequences.

Isolated plant promoters are useful in the genetic engineering of plants to produce transgenic plants with desired phenotypic characteristics. In order to produce such transgenic plants, an isolated plant promoter is inserted into a vector and operably linked to a heterologous DNA sequence. Plant cells can then be transformed in a variety of ways by DNA constructs containing an isolated plant promoter fused to heterologous DNA sequences. The result of this transformation is that the plant promoter operably linked to the heterologous DNA is inserted into the genome of the transformed plant cell. Furthermore, the regulation of the heterologous DNA in the transformed plant cell can be controlled by the expression of the promoter.

There are a variety of different approaches for producing a desired phenotype in a transgenic plant, depending on the nature of the heterologous sequences coupled to the isolated plant promoter. For example, expression of a novel gene that is not normally expressed in plant or in a particular tissue of a plant may confer a phenotypic change. Alternatively, the expression of a sense or an anti-sense construct introduced into transgenic plants can cause the inhibition of expression of endogenous plant genes. This inhibition of expression can, in turn, produce the desired phenotypic change.

There is a need for a variety of different promoters to be used in the genetic engineering of plants. These promoters are of several types. Constitutive promoters are one such commonly used type of promoter. Constitutive promoters are those which are capable of expressing operably linked DNA sequences in all tissues of a plant throughout normal development. In contrast to constitutive promoters, tissue-specific promoters are those promoters that are capable of selectively expressing heterologous DNA sequences in certain plant tissues. Tissue-specific promoters may also be inducible, e.g., by application of external inducing agents. Constitutive and tissue-specific promoters are both used in the genetic engineering of plants, and have value for many different potential applications in this field.

Constitutive plant promoters may be obtained by isolating the regulatory region of a plant gene that is constitutively expressed. In addition to promoters obtained from plant genes, there are also promoters of bacterial and viral origin which have been used to constitutively express novel sequences in plant tissues. Examples of such promoters from bacteria include the octopine synthase (ocs) promoter, the nopaline synthase (nos) promoter and others derived from native Ti plasmids (see Herrara-Estrella et al. (1983) *Nature* 303:209–213). The 35S and 19S RNA promoters of cauliflower mosaic virus are commonly used examples of viral promoters (see Odel et al. (1985) *Nature* 313:810–812).

In contrast to constitutive promoters, tissue-specific promoters are generally isolated from the promoter regions of plant genes that are selectively expressed in a specific plant tissue. These promoters can be fused with a heterologous DNA sequence and used to transform a plant cell to create transgenic plants that selectively express the heterologous DNA in a specific tissue. For example, the promoter regions from the fruit-specific, ethylene regulated genes E4 and E8 and from the fruit-specific polygalacturonase gene have been used to direct fruit specific expression of a heterologous DNA sequence in transgenic tomato plants. (See Cordes et al., *Plant Cell* (1989) 1;1025–1034, Deikman and Fischer, *EMBO J.* (1988) 7;3315–3320 and Della Penna et al., *Proc. Natl. Acad. Sci. USA* (1986) 83:6420–6424.)

The discovery of both new constitutive promoters and new tissue-specific promoters is desired for the controlled expression of various nucleic acid sequences that are genetically engineered into transgenic plants. There are many valuable potential applications of genetic engineering of plants. A variety of plant promoters with different characteristics and which are effective in different species of plants is desirable in order to bring these potential applications into practice.

SUMMARY OF THE INVENTION

The present invention provides for nucleic acids that hybridize under stringent conditions to a nucleic acid encoding a plant Gp2 protein having the amino acid sequence depicted in SEQ ID NO:1 or SEQ ID NO:2. In one embodiment, the amino acid sequence is depicted in SEQ ID NO:1 or SEQ ID NO:2. In another embodiment, the nucleic acid sequence is depicted in SEQ ID NO:1. In addition, the invention provides for the nucleic acids described above operably linked to a plant promoter. The plant promoter can be a heterologous promoter or Gp2 promoter capable of constitutive or tissue-specific expression. Preferentially, the above-described nucleic acid is from the Solanaceae family. More preferably, the nucleic acid is from a pepper plant.

The invention also provides for a recombinant expression cassette encoding the above-described nucleic acid operably linked to a plant promoter, either a heterologous promoter or a plant Gp2 promoter. The invention further provides for transgenic plants having the nucleic acid described above. In one embodiment, the transgenic plant includes a heterologous promoter or a Gp2 promoter linked to the above-described nucleic acid. In another embodiment, the transgenic plant is from the Solanaceae family. Preferably, the transgenic plant is a pepper or tomato plant. Furthermore, the nucleic acid included in the transgenic plant may be from a pepper plant.

In addition, the present invention provides for an isolated plant Gp2 promoter containing a nucleic acid sequence that is either identical to or which has substantial sequence identity to the nucleic acid sequence depicted in SEQ ID NO:4. Preferentially, the Gp2 promoter is from a member of the family Solanaceae. More preferably, the Gp2 promoter is from the genus Solanum of the family Solanaceae. The promoter can be, for example, from a pepper plant. The Gp2 promoter can be, for instance, either constitutive or tissue-specific. Constitutive Gp2 promoters typically are from about 250 to about 1,250 nucleotides in length. A preferred constitutive Gp2 promoter is about 1,233 nucleotides in length. An example of such a constitutive promoter is shown as SEQ ID NO:4. Tissue-specific Gp2 promoters are typically from about 1,500 to about 3,500 nucleotides in length. Tissue-specific promoters of the invention comprise a nucleic acid sequence that is identical to or which has substantial sequence identity to the Gp2 promoter sequence contained in plasmid PEP4-2GUS. A preferred a tissue-specific Gp2 promoter is about 2,700 nucleotides in length. An example of such a promoter is the Gp2 promoter sequence contained in plasmid PEP4-2GUS.

In addition to the above described promoter sequences, the present invention also provides for a vector having a plant Gp2 promoter operably linked to a heterologous nucleic acid sequence. The promoter in such a vector contains a nucleic acid sequence that is either identical to or has substantial sequence identity to the nucleic acid sequence shown as SEQ ID NO:4. The vector preferentially contains a promoter from the family Solanaceae and more preferably from the genus Solanum. For instance, the promoter can be from a pepper plant. The Gp2 promoter in the vector can be, for example, either constitutive or tissue-specific. A tissue-specific Gp2 promoter can have a nucleic acid sequence that is identical to or which has substantial sequence identity to the Gp2 promoter sequence contained in plasmid PEP4-2GUS. An example of a constitutive promoter is shown as SEQ ID NO:4. An example of a tissue-specific Gp2 promoter that can be used in the vector is the promoter sequence contained in plasmid PEP4-2GUS.

The present invention also provides for expression cassettes that have a Gp2 promoter operably linked to a heterologous nucleic acid sequence. The Gp2 promoter in the expression cassette contains a nucleic acid sequence that is either identical to or which has substantial sequence identity to the nucleic acid sequence depicted in SEQ ID NO:4. The expression cassette preferentially contains a Gp2 promoter from the family Solanaceae and more preferably from the genus Solanum. For instance, the promoter can be from a pepper plant. The Gp2 promoter in the expression cassette can be, for example, either constitutive or tissue-specific. An example of such a constitutive promoter is shown as SEQ ID NO:4. A tissue-specific Gp2 promoter can have a nucleic acid sequence that is identical to or which has substantial sequence identity to the Gp2 promoter sequence contained in plasmid PEP4-2GUS. An example of a tissue-specific Gp2 promoter that can be used in an expression cassette is the promoter sequence contained in plasmid PEP4-2GUS.

The present invention also provides for an isolated plant Gp2 gene or gene fragment having a plant Gp2 promoter operably linked to a nucleic acid sequence encoding a plant Gp2 protein. The plant Gp2 protein has an amino acid sequence that is either identical to or which has substantial sequence identity to the amino acid sequence depicted in SEQ ID NO:2. Preferentially, the plant Gp2 protein is from the family Solanaceae and more preferably from the genus Solanum. For instance, the Gp2 protein can be from a pepper plant. The pepper plant Gp2 amino acid sequence can be, for instance, the amino acid sequence of SEQ ID NO:2. The isolated plant Gp2 gene or gene fragment can have, for example, the nucleic acid sequence depicted in Seq. ID No. 3.

In addition to nucleic acids, vectors and expression cassettes, the present invention also provides for transgenic plants that have a plant Gp2 promoter operably linked to a heterologous nucleic acid sequence. This Gp2 promoter contains a nucleic acid sequence identical to or with substantial sequence identity to the nucleic acid sequence depicted in SEQ ID NO:4. The heterologous DNA sequence can be expressed, for example, constitutively or in a tissue specific manner in the transgenic plant. For constitutive expression, the Gp2 promoter can have, for instance, the nucleic acid sequence depicted in SEQ ID NO:4. For tissue-specific expression, including expression of the heterologous DNA sequence selectively in fruit tissue of the transgenic plant, the promoter can have a nucleic acid sequence that is identical to or which has substantial sequence identity to the nucleic acid sequence of the Gp2 promoter contained in plasmid PEP4-2GUS. For tissue specific expression, the Gp2 promoter can be, for example, the Gp2 promoter contained in plasmid PEP4-2GUS. The transgenic plant is preferably a member of the family Solanaceae and more preferably a member of the genus Solanum. Transgenic plants can be, for instance, pepper plants, tomato plants, and tobacco plants.

The present invention also provides for methods of expressing heterologous DNA sequences in plant cells. In these methods, a plant cell is transformed with a vector that has a Gp2 promoter operably linked to a heterologous nucleic acid sequence. After transformation with the vector, the plant cell is grown under conditions where heterologous nucleic acid sequences are expressed. The Gp2 promoter used in these methods contains a nucleic acid sequence identical to or with substantial sequence identity to the nucleic acid sequence depicted in SEQ ID NO:4. This Gp2 promoter can be, for example, a constitutive promoter or a tissue-specific promoter. A constitutive Gp2 promoter can have, for example, the nucleic acid sequence depicted in SEQ ID NO:4. A tissue specific promoter can have a nucleic acid sequence that is identical to or which has substantial sequence identity to the Gp2 promoter sequence contained in plasmid PEP4-2GUS. A tissue specific promoter can be, for instance, the Gp2 promoter contained in plasmid PEP4-2GUS. The plant cell of this method is preferably from a member of the family Solanaceae and more preferably from the genus Solanum. For instance, the plant cell can be a pepper plant cell, a tomato plant cell or a tobacco plant cell.

DEFINITIONS

Figure 1:
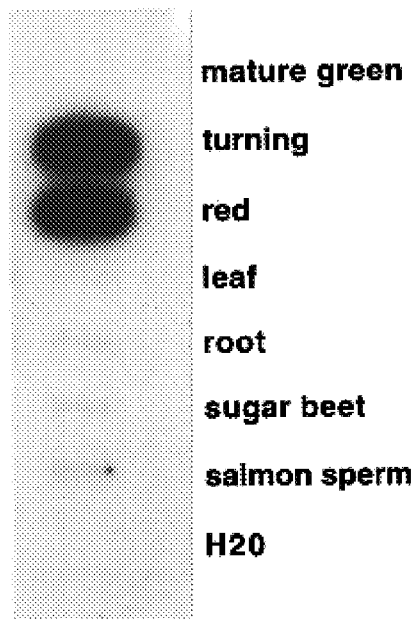
FIG. 1. RNA slot blot hybridized to $^{32}P$ Gp2 cDNA. Ten μg of total RNA isolated from pepper tissue from green fruit, turning fruit, red fruit, leaf and root was applied to a nylon filter using a slot blot apparatus and hybridized to $^{32}P$ labeled Gp2 CDNA. Total sugar beet RNA and salmon sperm DNA were used a negative controls.

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes self-replicating plasmids, infectious polymers of DNA or RNA and nonfunctional DNA or RNA.

In the polynucleotide notation used herein, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "promoter" refers to a region of DNA upstream from the translational start codon and which is involved in recognition and binding of RNA polymerase and other proteins to initiate transcription. A "plant promoter" is a promoter capable of initiating transcription in plant cells. The terms "Gp2 plant promoter" or "Gp2 promoter" as used herein refer to plant promoters derived from the promoter region of a plant Gp2 gene.

The terms "constitutive promoter or constitutive plant promoter" as used herein refer to a plant promoter which is capable of expressing operably linked DNA sequences in all tissues or nearly all tissues of a plant during normal development. The short form of the Gp2 promoter, as described herein, is an example of a constitutive promoter. The terms "inducible promoter" or inducible plant promoter", as used herein, refer to plant promoters that are capable of selectively expressing operably linked DNA sequences at particular times in response to endogenous or external stimuli.

The term "tissue-specific promoter" as used herein refers to plant promoters that are capable of selectively expressing operably linked DNA sequences, in particular plant tissues. This means that the expression of the operatively linked DNA sequences is higher in one or several plant tissues than it is in the other tissues of the plant. For example, the long form of the Gp2 promoter is a tissue-specific promoter that selectively expresses operably linked DNA sequences in fruit tissue during ripening.

The term "operably linked" as used herein refers to linkage of a promoter upstream from a DNA sequence such that the promoter mediates transcription of the DNA sequence. It is understood that the promoter sequence also includes transcribed sequences between the transcriptional start and the translational start codon.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "vector", refers to viral expression systems and autonomous self-replicating circular DNA (plasmids). Where a recombinant microorganism or cell culture is described as hosting an "expression vector," this includes extrachromosomal circular DNA or DNA that has been incorporated into the host chromosome(s), or both. Where a vector is being maintained by a host cell, the vector can either be stably replicated by the cells during mitosis as an autonomous structure, or incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes both extra-chromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

A "heterologous sequence" or a "heterologous DNA sequence", as used herein, is one that originates from a foreign source (or species) or, if from the same source, is modified from its original form. Thus, a heterologous DNA encoding sequence operably linked to a promoter is from a source different from that from which the promoter was derived, or, if from the same source, is modified from its original form. Modification of the heterologous DNA sequence may occur, e.g., by treating the DNA with a restriction enzyme to generate a DNA fragment that is capable of being operably linked to the promoter. Modification can occur by techniques such as site-directed mutagenesis.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987).

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. For example, the term "a nucleic acid encoding a plant Gp2 protein" includes those nucleic acid sequences which encode non-full length amino acid sequences derived from the full-length Gp2 protein. It being further understood that the sequence includes the degenerate codons of the native sequence or sequences which may be introduced to provide codon preference in a specific host cell.

The phrase "isolated" or "substantially pure" when referring to nucleic acid sequences encoding Gp2 proteins, refers to isolated nucleic acids that do not encode proteins or peptides other than Gp2 proteins. When referring to Gp2 promoter sequences, the terms "isolated" or "substantially pure" refer to isolated nucleic acids that contain promoter sequences from a Gp2 gene, but which do not contain promoter sequences from other genes.

The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "transgenic plant" refers to a plant that has been produced by genetic engineering techniques. For example, plant cells transformed with vectors containing Gp2 promoters operably linked to heterologous DNA sequences can be used to produce transgenic plants with altered phenotypic characteristics.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as the nucleic acid sequence or may comprise a complete cDNA or gene sequence.

Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.). Default parameters may be used to perform the sequence alignment.

The terms "substantial identity" or "substantial sequence identity" as applied to nucleic acid sequences and as used herein denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the Gp2 gene coding region or promoter regions, both disclosed herein.

As applied to polypeptides, the terms "substantial identity" or "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

DETAILED DESCRIPTION

This invention provides for isolated plant Gp2 cDNA and genomic DNA constructs. This invention also provides for isolated plant Gp2 promoters and for DNA constructs containing a Gp2 promoter operably linked to heterologous DNA sequences. Gp2 promoters may be either Gp2(short) promoters, which are constitutive, or Gp2(long) promoters which are tissue-specific. Both forms of Gp2 promoters are useful in the production of transgenic plants. Desired phenotypes are produced in transgenic plants as a result of transformation of plant cells by a DNA construct containing heterologous DNA sequence operably linked to a Gp2 promoter.

A. Isolation of Plant Gp2 Promoters

This invention relates to isolated cDNA and genomic DNA molecules encoding plant Gp2 proteins. The invention also relates to isolated plant Gp2 promoters and recombinant DNA constructs containing the Gp2 promoter. These DNA constructs include expression cassettes and a variety of vectors.

1) cDNA and Genomic DNA Encoding Plant Gp2 Proteins

Nucleic acid sequences encoding plant Gp2 proteins are typically identical to or show substantial sequence identity (determined as described above) to the nucleic acid sequence encoding the pepper plant Gp2 protein depicted in SEQ ID NO:1. (SEQ ID NO:1 is a cDNA sequence encoding a pepper plant Gp2 protein.) Nucleic acids encoding plant Gp2 proteins will typically hybridize to the nucleic acid sequence of Seq. ID No. 1 under stringent conditions. For example, high stringency hybridization can be done in buffer containing 50% formamide, 10% dextran sulfate, 10×Denhardts, 100 µg/ml salmon sperm, 1% SDS, 50 mM NaPO4, and 0.6M NaCl at 42° C. Filters are subsequently washed at 65° C. in 0.1×SSC, 0.1% SDS. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Plant Gp2 proteins appear to form a multigene (two or more) family in pepper plants. Plant Gp2 proteins typically show substantial sequence identity (as defined above) to the amino acid sequence of the pepper Gp2 protein as depicted in SEQ ID NO:2.

Techniques for nucleic acid manipulation of genes encoding plant Gp2 proteins such as subcloning nucleic acid sequences encoding polypeptides into expression vectors, labelling probes, DNA hybridization, and the like are described generally in Sambrook, et al., *Molecular Cloning—A Laboratory Manual* (2nd Ed.), Vol. 1–3, Cold Spring Harbor Laboratory, Cold Spring Harbor, N.Y., 1989, which is incorporated herein by reference. This manual is hereinafter referred to as "Sambrook, et al."

There are various methods of isolating DNA sequences encoding plant Gp2 proteins. For example, DNA is isolated from a genomic or cDNA library using labelled oligonucleotide probes having sequences complementary to the sequences disclosed herein (see SEQ ID NOS:1 and 3). SEQ ID NO:1 is a cDNA sequence which encodes a pepper Gp2 protein. (The predicted amino acid sequence for the pepper Gp2 protein is shown in SEQ ID NO:2.) SEQ ID NO:3 is a genomic DNA sequence which includes a short form of a Gp2 promoter, the first exon and a part of the first intron. Full-length probes may be used, or oligonucleotide probes may also be generated by comparison of the sequences of SEQ ID NOS:1 and 3. Such probes can be used directly in hybridization assays to isolate DNA encoding plant Gp2 proteins. Alternatively, probes can be designed for use in amplification techniques such as PCR, and DNA encoding plant Gp2 proteins may be isolated by using methods such as PCR (see below).

To prepare a cDNA library, mRNA is isolated from a plant tissue which expresses a Gp2 protein. For instance, the pericarp tissue of the fruit of a plant can be used. cDNA is prepared from the mRNA and then a second, complementary DNA strand is synthesized. Subsequently, this duplex DNA molecule is ligated into a recombinant vector. The vector is transfected into a recombinant host for propagation, screening and cloning. Methods for making and screening cDNA libraries are well known. See Gubler, U. and Hoffman, B. J. *Gene* 25:263–269, 1983 and Sambrook, et al.

For a genomic library, typically the DNA is extracted from plant tissue and either mechanically sheared or enzymatically digested to yield fragments of about 15–20 kb. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in Benton and Davis, *Science,* 196:180–182 (1977). Colony hybridization is carried out as generally described in M. Grunstein et al. *Proc. Natl. Acad. Sci. USA.,* 72:3961–3965 (1975). DNA encoding plant Gp2 proteins is identified in either cDNA or genomic libraries by its ability to hybridize with nucleic acid probes, for example on Southern blots, and these DNA regions are isolated by standard methods familiar to those of skill in the art. See Sambrook, et al. See also Example 4, herein, for a description of the isolation of a pepper Gp2 gene.

The term "plant Gp2 gene" or "Gp2 gene" as used herein refers to a plant genomic DNA molecule that is the entire Gp2 promoter region operably linked to the entire coding region (including exons and introns) for the Gp2 protein and may include the adjacent 3' flanking region which encodes the 3' non-translated mRNA. The term "plant Gp2 gene fragment" or "Gp2 gene fragment" refers to a portion of the plant Gp2 gene which is less than the entire promoter and coding regions of the gene. A plant Gp2 gene fragment may be composed of a promoter region operably linked to a portion of the coding region of the gene. An example of a plant Gp2 gene fragment from pepper is shown in SEQ ID NO:3.

Nucleic acid amplification techniques such as polymerase chain reaction (PCR) technology, can be used to amplify nucleic acid sequences encoding Gp2 proteins from mRNA, from cDNA, and from genomic libraries or cDNA libraries. In PCR techniques, oligonucleotide primers complementary to the two 3' borders of the DNA region to be amplified are synthesized. The polymerase chain reaction is then carried out using the two primers. See *PCR Protocols: A Guide to Methods and Applications* (Innis, M, Gelfand, D., Sninsky, J. and White, T., eds.), Academic Press, San Diego (1990). Primers can be selected to amplify the entire regions encoding a full-length Gp2 protein or its promoter. PCR can also be used to amplify smaller DNA segments of these regions as desired.

PCR and related amplification techniques can be used in a number of ways to isolate cDNA and DNA molecules encoding Gp2 proteins. For example, PCR can be used in a variety of protocols to isolate cDNAs encoding Gp2 proteins. In these protocols, appropriate primers and probes for amplifying DNA encoding plant Gp2 proteins are generated from analysis of the DNA sequences listed herein.

Oligonucleotides for use as probes in the above-mentioned procedures can be chemically synthesized according to the solid phase phosphoramidite triester method first described by Beaucage, S. L. and Carruthers, M. H., 1981, *Tetrahedron Lett.,* 22(20):1859–1862 using an automated synthesizer, as described in Needham-VanDevanter, D. R., et al., 1984, *Nucleic Acids Res.,*

12:6159–6168. Purification of oligonucleotides is by either native acrylamide gel electrophoresis or by anion-exchange HPLC as described in Pearson, J. D. and Regnier, F. E., 1983, *J. Chrom.*, 255:137–149. The sequence of the synthetic oligonucleotide can be verified using the chemical degradation method of Maxam, A. M. and Gilbert, W. 1980, in Grossman, L. and Moldave, D., eds. Academic Press, New York, *Methods in Enzymology*, 65:499–560.

2) Plant Gp2 Promoters

Plant Gp2 promoter sequences are typically identical to or show substantial sequence identity (determined as described above) to the pepper plant Gp2 promoter nucleic acid sequence depicted in SEQ ID NO:4. SEQ ID NO:4 depicts the nucleotide sequence of a long form of the pepper Gp2 promoter. Plant Gp2 promoter sequences typically hybridize to the nucleic acid sequence of SEQ ID NO:4 under stringent conditions. For example, high stringency hybridization can be done in buffer containing 50% formamide, 10% dextran sulfate, 10×Denhardts, 100 µg/ml salmon sperm, 1% SDS, 50 mM NaPO4, and 0.6M NaCl at 42° C. Filters are subsequently washed at 65° C. in 0.1×SSC, 0.1% SDS. Other stringent hybridization conditions such as those described above for cDNA and genomic DNA encoding plant Gp2 proteins may also be selected.

Plant Gp2 promoters can be isolated in a variety of ways. Since Gp2 protein is a member of a multigene family, a number of different Gp2 promoters having homology or substantial sequence identity to the Gp2 promoter sequence of SEQ ID NO:4 may be isolated from pepper plants. In addition, Gp2 promoters may be isolated from a variety of other plant species, in particular, other Solanaceae species.

There are a variety of methods known to those of skill in the art which may be used for isolation of plant Gp2 promoters. For example, plant Gp2 promoters can be isolated from genomic DNA fragments encoding a plant Gp2 protein and which also contain sequences upstream from the sequence encoding the Gp2 protein. Genomic fragments encoding plant Gp2 proteins can be isolated as described above. See Example 4, herein, for a demonstration of the isolation of Gp2 promoter sequences from genomic DNA fragments which encode pepper Gp2 proteins.

Plant Gp2 promoter sequences can also be isolated by screening plant DNA libraries with oligonucleotide probes having sequences derived from the DNA sequence of the pepper Gp2 promoter depicted in SEQ ID NO:4. The various methodologies described above for isolation of genomic DNA fragments encoding a Gp2 protein can also be used for the isolation of Gp2 promoters using the Gp2 promoter sequence of SEQ ID NO:4. Other methods known to those of skill in the art can also be used to isolate plant DNA fragments containing Gp2 promoters. See Sambrook, et al. for a description of other techniques for the isolation of DNAs related to DNA molecules of known sequence.

Different forms of a Gp2 promoter can be produced that have different properties. For example, short forms of Gp2 promoters control constitutive expression of DNA sequences that are operably linked to the promoter. Short forms of a Gp2 promoter which regulate constitutive expression are typically from 250 to 1250 nucleotides in length. An example of a short form of a Gp2 promoter 1233 nucleotides in length is shown in SEQ ID NO:4.

Short forms of a Gp2 promoter can be constructed in a variety of ways known to those of skill in the art. For example, short forms of Gp2 promoters can be constructed by mapping restriction enzyme sites in the promoter and then using the constructed map to determine appropriate restriction enzyme cleavage to excise a subset of the sequence. The shorter restriction fragment can then be inserted into a suitable vector. The construction of a specific short form of a Gp2 promoter which controls constitutive expression of operably linked heterologous DNA sequences is shown in Example 4, herein. Other short forms of the Gp2 promoter that are constitutive can also be prepared in a similar fashion.

Short forms of a Gp2 promoter can be shown to express operably linked heterologous DNA sequences in a constitutive fashion. This can be done by first preparing a vector that has a short form of the Gp2 promoter operably linked to an indicator gene. Plant cells are then transformed with the vector and transgenic plants are produced from the transformed plant cells. Expression of the indicator gene under the control of the Gp2 promoter is then determined. See Examples 6–12 herein for a demonstration of the constitutive expression of a heterologous DNA sequence by the short form of a Gp2 promoter.

Long forms of Gp2 promoters that are tissue-specific promoters may also be isolated, using techniques similar to those used for isolation of short forms of the Gp2 promoter. Long forms of a Gp2 promoter typically contain from 1,500 to 3,500 nucleotides. An example of a long form of a Gp2 promoter, containing about 2,700 nucleotides, and which is obtained from a pepper plant, is described in Example 16 herein.

Long forms of Gp2 promoters can also be constructed in a variety of ways. For example, construction of long forms of Gp2 promoters that regulate tissue-specific expression of operably linked heterologous sequences can be performed by using restriction enzymes, as described above for the construction of short forms Gp2 promoters. Long forms of Gp2 promoters can also be constructed by adding additional sequences to a short Gp2 promoter, using procedures similar to those described in Example 13, herein.

Long forms of the Gp2 promoter can be shown to selectively express operably linked heterologous DNA sequences in fruit tissue of transgenic plants. This can be done as described above for the short forms of the Gp2 promoter. See Examples 14–18, herein, for a demonstration of the operation of a long form of a Gp2 promoter in selectively expressing operably linked heterologous DNA sequences in transgenic plants.

B. Construction of Vectors Containing a Gp2 Promoter Operably Linked to a Heterologous DNA Sequence Once a plant Gp2 promoter region has been isolated, various methods may be used to construct long and short forms of the promoter. These different forms of the Gp2 promoter can then be used in expression cassettes, vectors and other DNA constructs. A variety of techniques can be used for these manipulations of nucleic acids. These techniques are known to those of skill in the art and are described generally in Sambrook, et al., supra.

Expression cassettes containing a Gp2 promoter can be constructed in a variety of ways. For instance, various procedures, such as site directed mutagenesis can be used to introduce a restriction site at the start codon of a Gp2 gene fragment (see Example 5, herein). Then heterologous DNA sequences can be linked to the Gp2 promoter such that the expression of the heterologous sequences is regulated by the promoter (see Examples 6, 9, and 11 herein for examples of procedures useful for operably linking heterologous DNA sequences to Gp2 promoters). DNA constructs composed of a Gp2 promoter operably linked to heterologous DNA sequences can then be inserted into a variety of vectors. Such vectors include expression vectors that are useful in the transformation of plant cells (see Examples 6, 9, 11, 13 and 16 herein, for a description of the production of several vectors containing a Gp2 promoter operably linked to a heterologous DNA sequence). Many other such vectors useful in the transformation of plant cells can be constructed by the use of recombinant DNA techniques well known to those of skill in the art.

C. Production of Transgenic Plants

1) Use of DNA Constructs Containing Gp2 Promoters to Produce Altered Phenotypes in Transgenic Plants DNA constructs containing a Gp2 promoter operably linked to a heterologous DNA sequence can be used to transform plant cells and produce transgenic plants with desired phenotypic characteristics. There are a variety of different approaches one can use to produce a desired phenotype in transgenic plants. For example, by using methods described herein, one can operably link a novel gene to a Gp2 promoter and transform plant cells. Transgenic plants can be produced from the transformed plant cells so that the novel gene product is produced in all tissues or in only certain tissues of a transgenic plant. In this context, the term "novel gene" refers to a gene that is not normally present in a plant or which, if present, is not normally expressed in a particular plant cell tissue. The expression of the novel gene can result in the production of a protein that confers an altered phenotype for a transgenic plant.

A mutant form of the ALS gene is of interest because it can be used in a wide range of plant species as a selectable marker in plant transformation protocols. Expression of the mutant ALS gene confers resistance to the herbicide chlorsulfuron (see Example 9, herein). The constitutive form of a Gp2 promoter has been fused to a mutant form of the ALS gene. Transformation of tomato and pepper plant cells with this DNA construct has been shown to result in expression of the ALS gene in the transformed plant cells (see Examples 9 and 10, herein). Thus, the mutant ALS gene, when introduced into plant cells and constitutively expressed, confers a phenotype that is useful in the production of transgenic plants.

A variety of other genes capable of altering a plant phenotype can also be expressed with a Gp2 promoter. For constitutive expression, the short form of the Gp2 promoter can be used operably linked to, e.g., genes for herbicide resistance; genes for fungal disease resistance (e.g., chitinases and glucanases); genes for bacterial disease resistance (e.g., cecropins); and genes for insect resistance (e.g., *B. thuringiensis* toxin). For tissue-specific expression, the long form of the Gp2 promoter can be used operably linked to, e.g., genes for ripening or degradation (e.g., Acc oxidase, Acc synthase, polygalacturonase, phytoene synthase); genes for color; or genes for sweetness.

One of skill will recognize that proteins have different domains which perform different functions. Thus, gene sequences operably linked to a Gp2 promoter need not be full length, so long as the desired functional domain of the protein is expressed. Modified protein chains can also be readily designed utilizing various recombinant DNA techniques well known to those skilled in the art. For example, the chains can vary from the naturally occurring sequence at the primary structure level by amino acid substitutions, additions, deletions, and the like. These modifications can be used in a number of combinations to produce the final modified protein chain.

DNA constructs containing a Gp2 promoter operably linked to a heterologous DNA sequence can also be used in a number of techniques to suppress expression of endogenous plant genes, e.g., sense or antisense suppression. In antisense technology, a nucleic acid segment from the desired plant gene is cloned and operably linked to a Gp2 promoter such that the anti-sense strand of RNA will be transcribed. The construct is then transformed into plants and the antisense strand of RNA is produced. In plant cells, it has been shown that anti-sense RNA inhibits gene expression; see, e.g., Sheehy et al., *Proc. Nat. Acad. Sci. USA*, 85:8805–8809 (1988), and Hiatt et al., U.S. Pat. No. 4,801, 340 which are incorporated herein by reference.

The nucleic acid segment to be introduced in antisense suppression generally will be substantially identical to at least a portion of the endogenous gene or genes to be repressed, but need not be identical. The vectors of the present invention can be designed such that the inhibitory effect applies to other proteins within a family of genes exhibiting homology or substantial homology to the target gene. Segments from a gene can be used (1) directly to inhibit expression of homologous genes in different plant species, or (2) as a means to obtain the corresponding sequences, which can be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2,000 nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes also have been reported to have use as a means to inhibit expression of endogenous plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozyme is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature*, 334:585–591 (1988), which is incorporated herein by reference.

A preferred method of suppression is sense suppression. Introduction of a nucleic acid configured in the sense orientation has been shown to be an effective means by which to block the transcription of target genes. For examples of the use of this method to modulate expression of endogenous genes see, Napoli et al., *The Plant Cell* 2:279–289 (1990), and U.S. Pat. No. 5,034,323, which are incorporated herein by reference. Sense suppression is a preferred method for ripening control (e.g., Acc oxidase or Acc synthase), sweetness control (e.g., ADPG pyrophosphorylase), or color modification (e.g., chalcone synthase); see U.S. Pat. No. 5,034,323.

Generally, in sense suppression, some transcription of the introduced sequence occurs. The effect may also occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity is useful to exert a more effective repression of expression of the endogenous sequences. Substantially greater identity of more than about 80% is preferred, though about 95% to absolute identity would be most preferred. The effect may be applied to other proteins within a similar family of genes exhibiting homology or substantial homology. Segments from a gene can be used (1) directly to inhibit expression of homologous genes in different plant species, or (2) as a means to obtain the corresponding sequences, which can be used to suppress the gene.

In sense suppression, the introduced sequence, needing less than absolute identity, also need not be full length, relative to either the primary transcription product or fully processed mRNA. A higher identity in a shorter than full length sequence compensates for a longer, less identical sequence. Furthermore, the introduced sequence need not have the same intron or exon pattern, and identity of non-coding segments may be equally effective. A sequence of a size of at least 50 base pairs is preferred, with greater length sequences being more preferred; see U.S. Pat. No. 5,034,323.

2) Transformation of Plant Cells and Production of Transgenic Plants

Techniques for transforming a wide variety of higher plant species are well known and described in the technical and scientific literature. See, for example, Weising et al. *Ann. Rev. Genet.* 22:421–477 (1988), which is incorporated herein by reference. As described herein, a constitutive or inducible Gp2 promoter is operably linked to the desired heterologous DNA sequence in a suitable vector. The vector comprising a Gp2 promoter fused to heterologous DNA will typically contain a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorsulfuron or Basta. Such selective marker genes are useful in protocols for the production of transgenic plants.

DNA constructs containing a Gp2 promoter linked to heterologous DNA can be introduced into the genome of the desired plant host by a variety of conventional techniques. For example, the DNA construct may be introduced directly into the genomic DNA of the plant cell using techniques such as electroporation and microinjection of plant cell protoplasts. Alternatively, the DNA constructs can be introduced directly to plant tissue using ballistic methods, such as DNA particle bombardment. In addition, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., *Embo J.* 3:2717–2722 (1984). Electroporation techniques are described in Fromm et al., *Proc. Natl. Acad. Sci. USA* 82:5824 (1985). Ballistic transformation techniques are described in Klein et al., *Nature* 327:70–73 (1987). The full disclosures of each of these references are incorporated herein by reference.

Another method is high velocity ballistic penetration by small particles with the nucleic acid either within the matrix of small beads or particles, or on the surface (Klein et al., (1987) *Nature* 327:70–73. Although typically only a single introduction of a new nucleic acid segment is required, this method particularly provides for multiple introductions.

*Agrobacterium tumefaciens*-meditated transformation techniques are well described in the scientific literature. See, for example Horsch et al. *Science* (1984) 233:496–498, and Fraley et al. (1983) *Proc. Natl. Acad. Sci. USA* 80:4803, both of which are incorporated herein by reference. See Examples 7, 9, 11, 14, and 17, herein, for a demonstration of the transformation of plant cells with a vector comprising a Gp2 promoter by *Agrobacterium tumefaciens*.

More specifically, a plant cell, an explant, a miristem or a seed is infected with *Agrobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," *Science,* 233:496–498; Fraley et al., (1983) *Proc. Nat'l. Acad. Sci. U.S.A.* 80:4803.

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector".

All plant cells which can be transformed by Agrobacterium and whole plants regenerated from the transformed cells can also be transformed according to the invention so as to produce transformed whole plants which contain the transferred foreign nucleic acid sequence.

There are various ways to transform plant cells with Agrobacterium, including:

(1) co-cultivation of Agrobacterium with cultured isolated protoplasts, (2) transformation of cells or tissues with Agrobacterium, or (3) transformation of seeds, apices or meristems with Agrobacterium.

Method (1) requires an established culture system that allows culturing protoplasts and plant regeneration from cultured protoplasts.

Method (2) requires (a) that the plant cells or tissues can be transformed by Agrobacterium and (b) that the transformed cells or tissues can be induced to regenerate into whole plants.

Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

The present invention embraces use of the claimed promoters in transformation of any plant, including both dicots and monocots. Transformation of dicots is described in references above. Transformation of monocots is known using various techniques including electroporation (e.g., Shimamoto et al., *Nature* (1992), 338:274–276; ballistics (e.g., European Patent Application 270,356); and Agrobacterium (e.g., Bytebier et al., Proc. Nat'l Acad. Sci. USA (1987) 84:5345–5349).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the Ph nucleotide sequences. Plant regeneration from cultured protoplasts is described in Evans et al., *Protoplasts Isolation and Culture, Handbook of Plant Cell Culture*, pp. 124–176, MacMillan Publishing Company, New York, 1983; and Binding, *Regeneration of Plants, Plant Protoplasts*, pp. 21–73, CRC Press, Boca Raton, 1985, all of which are incorporated herein by reference. Regeneration can also be obtained from plant callus, explants, organs, or parts thereof. Such regeneration techniques are described generally in Klee et al. *Ann. Rev. of Plant Phys.* 38:467–486 (1987), which is incorporated herein by reference.

One of skill will recognize that, after an expression cassette comprising the Gp2 promoter is stably incorporated in transgenic plants and confirmed to be operable, it can be introduced into other plants by sexual crossing. Any of a number of standard breeding techniques can be used, depending upon the species to be crossed.

The expression of the heterologous DNA sequences linked to a Gp2 promoter can be detected in a variety of ways, depending on the nature of heterologous sequences. For example, one may assay for the desired phenotype. The desired phenotype which results from the successful expression of heterologous DNA sequences under control of a Gp2 promoter may be determined by a variety of ways, depending on the phenotypic trait that is introduced. For instance, resistance to a herbicide can be detected by treatment with the herbicide.

Expression of the heterologous DNA can also be detected by measurement of the specific RNA transcription product. This can be done by, for example, RNAse protection or Northern blot procedures (see Examples 8, 10, 12, 15, and 18 herein). If heterologous DNA sequences encode a novel protein, the protein product may be assayed, for instance, by its function or by a variety of immunoassay techniques. For example, a novel protein product with enzymatic activity can be measured in an enzyme assay (see examples 8 and 15, herein).

The methods and compositions of the invention have use over a broad range of types of plants, including species from the genera Fragaria, Lotus, Medicago, Onobrychis, Trifolium, Trigonella, Vigna, Citrus, Linum, Geranium, Manihot, Daucus, Arabidopis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Herecocallis, Nemesia, Pelargonium, Panicum, Pennisetum, Ranunculus, Senecio, Salpiglossis, Cucumis, Browaalia, Glycine, Lolium, Zea, Triticurn, Sorghum, Datura, Chrysanthemum, Dianthus, Gerbera, Euphorbia, Ipomoea, Passiflora, Cyclamen, Malus, Prunus, Rosa, Rubus, Populus, Santalum, Allium, Lilium, Narcissus, Ananas, Arachis, Phaseolus and Pisum, and more particularly including oil crops such as canola (Brassica sp.), cotton (Gossypium sp.), peanut (Arachis sp.), sunflower (Helianthus sp.), palm (Elaeis sp.), flax (Linum sp.), safflower (Carthamus sp.), coconut (Cocos ap.) and soybean (Glycine sp.); grain crops such as wheat (Triticum sp.), corn (Zea sp.), sorghum (Sorghum sp.), barley (Hordeum sp.), rye (Secale sp.), oats (Avena sp.) and rice (Oryza sp.); fruit crops such as banana (Musa sp.), citrus (Citrus sp.), berries (e.g., strawberry (Fragaria Sp.) or raspberry (Rubus sp.), mango (Mangifera sp.), melon (Cucumis sp.), pear (Pyrus sp.), cucumber (Cucumis sp.), and apricot, peach, cherry, plum and prune (Prunus sp.); vegetable crops such as pea (Pisum sp.), bean (Vicia sp.), broccoli and related crucifers (Brassica sp.), spinach (spinacia sp.), onion (Allium sp.), celery (Apium sp.), carrot (Daucus sp.), asparagus (Asparagus sp.), and artichoke (Helianthus sp.); tomato (*Lycopersicon esculentum*), pepper (*Capiscum annuum*); additional ornamental crops such as tulip (Tulipa sp.), snapdragon (Antirrhinum sp.), Iris (Iris sp.), Orchids (Cymbidium and Cattleya sp.), pelargonium; beverage crops such as coffee (Coffea sp.) and tea (Thea sp.); herb crops such as mint (Mentha sp.), thyme (Thymus sp.) and marjoram (Origanum sp.).

The following examples are provided by way of illustration and not limitation.

EXAMPLES

Example 1

Isolation and Characterization of Gp2 cDNA Clones from Pepper Plants

Gp2 cDNA was obtained by the differential screening of a green pepper pericarp cDNA library with green fruit cDNA. The selected cDNA clone was subsequently shown to hybridize very strongly to pepper pericarp mRNA (from both green and red fruit) but to be absent in mRNA from leaf, root, flowers etc.

In order to isolate cDNA, pepper plants (*Capsicum annuum* cv D2XYBA) were grown under greenhouse conditions. Poly(A)$^+$ RNA was isolated from mature green fruit, red fruit and leaf (Dunsmuir et al., eds., (1988) *Plant Molecular Biology Manual*, S. Gelvin and R. Schilperoovt, Kluwer Academic Dordrecht, pp. 1–17). First strand cDNA was synthesized from the poly (A)+ RNA (extracted from both mature green fruit and red fruit) using oligo dT as the primer and reverse transcriptase. The second strand was synthesized using DNA polymerase I and RNAse H according to the manufacturers instructions (Amersham Little Chaflont, U.K.). The cDNA was modified with EcoRI methylase to inhibit digestion of internal EcoRI sites then ligated to EcoRI linkers. After cutting back with EcoRI to remove excess linkers, size selection was done using an acrylamide gel or Sephacryl S400 column and only those cDNAs greater than 500 bp were used. The double stranded cDNA was cloned into the EcoRI site of the lambda—ZAP vector (Stratagene, San Diego, Calif., USA) and packaged in vitro using Gigapack packaging extracts (Stratagene).

10,000 recombinant phage from the mature green fruit cDNA library (2000/85 mm plate) were plated using E. coli strain C600. The phage plaques were transferred onto nitrocellulose filters (filters were made in triplicate) and the phage DNA was denatured in 1.5 M NaCl, 0.5 N NaOH and neutralized in 1.5 M NaCl, 0.5 M Tris-HCl, pH8. The filters were screened with $^{32}$P radiolabeled cDNA made from red fruit mRNA, mature green fruit mRNA and leaf mRNA. Hybridization conditions and washes were essentially as described in Sambrook, et al., (1989) Molecular Cloning: a Laboratory Manual, Second Edition, Cold Spring Harbor Laboratory, New York.

Twelve plaques were selected which hybridized strongly with mature green fruit and red fruit cDNAs and not with leaf cDNA. DNA was purified from these selected phage for further analysis. The cDNA inserts were isolated from the recombinant phage by gel purification after restriction digestion with EcoRI. The inserts were subcloned into the EcoRI site of the plasmid pGEM7 (Promega Corporation, Madison, Wis., USA).

Figure 2:
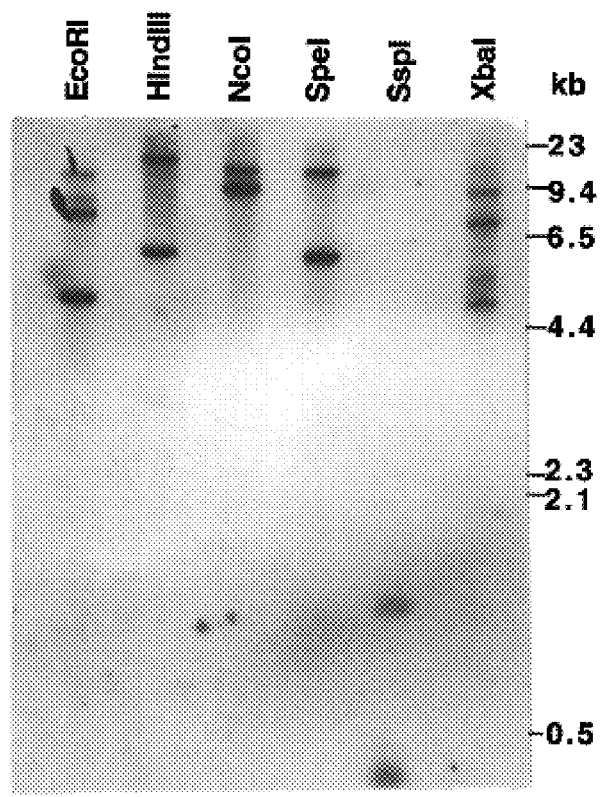
FIG. 2. Genomic Southern hybridization of pepper DNA with $^{32}P$ Gp2 cDNA. 10 μg of genomic pepper DNA was digested with restriction enzymes EcoRI (E), HindIII (HIII), NcoI (N), SpeI (Sp), SspI (S) and XbaI (X) and separated on an agarose gel. The DNA was transferred to a nylon membrane and hybridized to $^{32}P$ labelled Gp2 cDNA.

The plasmid clones were first used in cross-hybridization experiments to determine if they were related to each other. 0.5–1 μg of EcoRI digested plasmid DNA from each cDNA clone was run in parallel on an agarose gel, transferred to a Duralon nylon membrane (Stratagene, San Diego, Calif., USA) and hybridized to nick translated $^{32}$P labeled probes prepared from each of the cDNA clones. Plasmid cloning, Southern transfer, probe preparation and hybridizations were done as described in Sambrook et al., Supra (1989). Based upon the cross hybridization pattern, the clones were placed into four separate homology groups numbered Groups 1 to 4. The longest cDNA from each homology group was then used as a probe in Northern hybridizations to total RNA isolated from leaf, root, green fruit and red fruit, and as a probe for slot blots prepared from total RNA isolated from pepper fruit at different stages of development (days after anthesis). For Northern blots, 10 μg of total RNA was separated on a 1.5% agarose/formaldehyde gel and transferred to a nylon membrane. 10 μg of total RNA was treated in 6% formaldehyde/50% formamide at 50 C. for 60 minutes before loading onto the nylon filter. The Northern blots and slot blots were prepared and hybridized to $^{32}$P nick-translated cDNA probes as described in Sambrook et al., (1989), supra. cDNAs in group 1 (Gp1) and group 3 (Gp3) hybridized to fruit and root RNA while those in group 2 (Gp2) and group 4 (Gp4) gave fruit specific hybridization. The Gp2 clones hybridized to a 700–800 base transcript which was expressed primarily in mature fruit (see FIG. 1). The Gp4 clones hybridized to a 900–1000 base transcript which was expressed at moderate levels throughout fruit development. In view of these expression profiles, all subsequent analysis was confined to the Gp2 cDNA clones. The mature green fruit cDNA library and the red fruit cDNA library was rescreened with the pGP23 cDNA in order to isolate and characterize related cDNAs for the purpose of establishing whether multiple genes were being transcribed in the mature fruit tissue or whether all transcripts derived from a single gene. The hybridization patterns indicated that the Gp2 transcripts were derived from genes which were part of a small multigene family in the pepper genome (See FIG. 2).

Once the cDNA clone was demonstrated to be expressed at a high level in the fruit, the nucleotide sequence of the cDNA was determined. Sixteen independent Gp2 cDNAs were isolated from the lambda ZAP libraries. The cDNA inserts were excised from the lambda clones as EcoR1 fragments and these were recloned into the vector BS(+) (Stratagene, San Diego, Calif., USA) which is suitable for preparation of single strand templates for gene expression and sequencing studies. These clones were sequenced from both the 5' and 3' end by the Sanger dideoxy chain termination method. All 16 clones were found to be identical in primary sequence except for the position of the polyadenylation sites, and the number of A residues in A-tracks at the extreme 5' end of the clones. A common feature of plant genes is that transcripts from a single gene will have variability in the polyadenylation site; see Dean et al., (1986), Nucl. Acid. Res. 14:2229–2240. Transcripts from a single gene may also have extreme 5' end differences in the number of A residues in A-tracks; this is a common artifact of cDNA synthesis. These data suggest that the Gp2 transcripts arise from a single gene. When the 16 clones were aligned, pGP13 had the longest 3' and pGP50 had the longest 5' sequence; pGP13 was completely sequenced; pGP50 was sequenced across the 5' end which overlapped with pGP13. The composite cDNA sequence is shown in SEQ ID NO:1.

The pGP13 sequence was translated in three frames and the longest open reading frame (beginning with the first ATG) is designated as such in SEQ ID NO:1. The cloned cDNA fragment encodes a 75 amino acid polypeptide which is highly enriched in the sulphur containing amino acids. This predicted amino acid sequence is shown as SEQ ID NO:2. A comparison of the predicted protein sequence to sequences in EMBL Genbank shows some homology to proteins similar to the Bowman Birk proteinase inhibitors, as well as thionins, and a-amylase inhibitors.

Example 2
Genomic DNA Encoding Gp2 Proteins in Pepper Plants

Genomic DNA encoding Gp2 proteins was identified in pepper plants by Southern blot analysis. Genomic Southern analysis was performed as described by Sambrook et al., supra 1989. Genomic pepper DNA was isolated from cultivar D2XYBA according to the method of Dooner et al., (1985) Mol. Gen. Genet. 200:240–246 and digested with EcoRI, HindIII, and XbaI. The digested DNA was separated on an agarose gel and transferred to Duralon membrane (Stratagene, San Diego, Calif., USA). The membrane was hybridized to a $^{32}$P in vitro labeled RNA riboprobe prepared from pGP23 (Gp2 cDNA clone). High stringency hybridization was done in buffer containing 50% formamide, 10% dextran sulfate, 10×Denhardts, 100 μg/ml salmon sperm, 1% SDS, 50 mM NaPO4, and 0.6M NaCl. at 42° C. Filters were subsequently washed at 65° C. in 0.1×SSC, 0.1% SDS.

Example 3
Expression of Gp2 Genes in Pepper Plants

To determine the distribution of Gp2 gene expression in pepper, RNAse protections and primer extensions were done on total RNA isolated from different pepper tissue. A 294 bp internal HincII fragment from pGp13 was purified on an agarose gel and cloned into the BS(+) vector (Stratagene San Diego, Calif., USA) to form the plasmid pGp13-1. This clone was used in the preparation of in vitro labeled riboprobe for RNAse protection experiments and screening of the genomic DNA library (see below). A 20 base oligonucleotide shown below, beginning 19 bp downstream of the translation start was prepared for the primer extension analysis.

5' CTACTTTGGAAAAGCCAGCC 3'    (SEQ ID NO:5)

Figure 3:
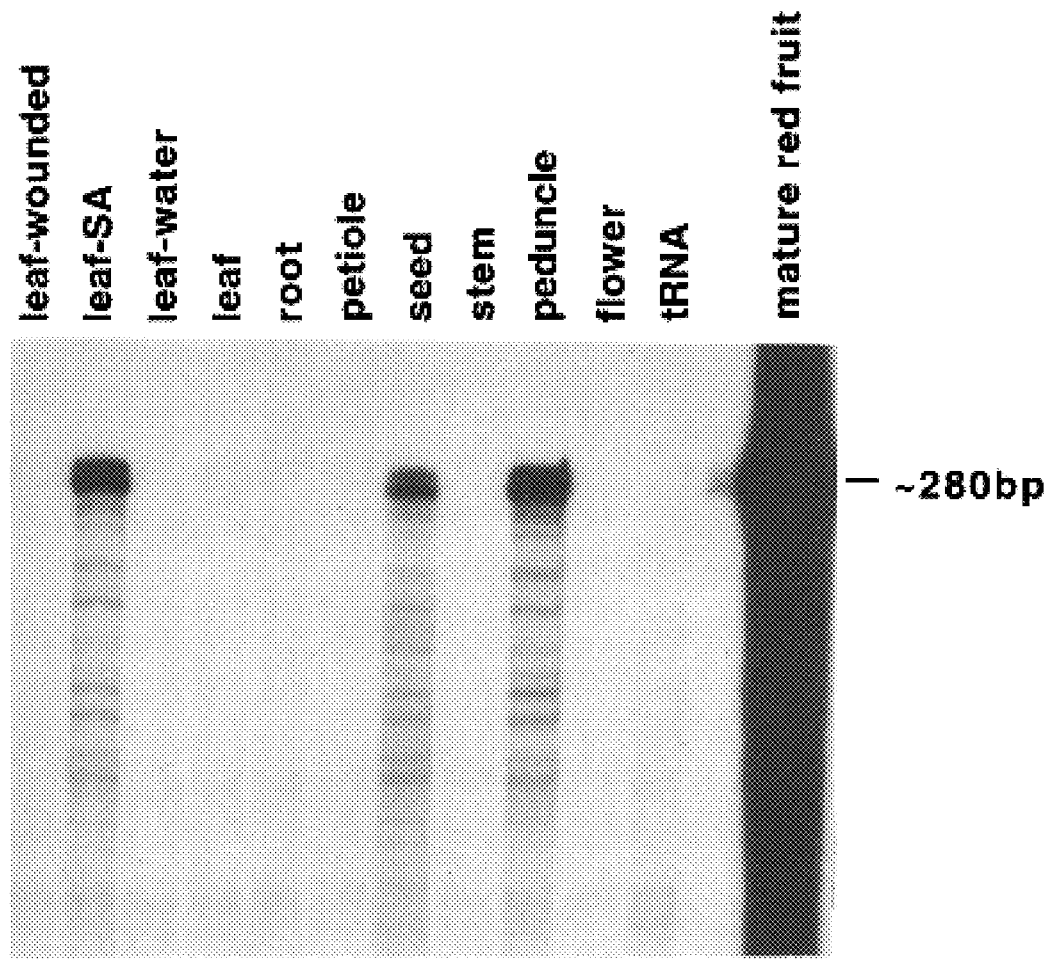
FIG. 3. RNAse protection analysis on total RNA prepared from pepper. Total RNA was isolated from the indicated plant tissues without pretreatment. Total RNA was also isolated from pretreated leaf tissue. For the pretreated leaf tissue, total RNA was isolated 24 hours after wounding, after 24 hours in 0.01% salicylic acid or after 24 hours in water. For all tissues, 10 µg of RNA was hybridized to the $^{32}P$ labeled Gp2 riboprobe, the hybrids were digested with RNAse A and T1 and the protected fragments were separated on a 6% acrylamide urea gel.

Primer extensions were done on 10 μg of total RNA isolated from leaf, stem, petiole, root, seed, peduncle and flower and pepper fruit from different developmental stages according to the method described by Dunsmuir et al., eds., (1988) *Plant Molecular Biology Manual,* S. Gelvin and R. Schilperoovt, Kluwer Academic Dordrecht, pp. 1–17. RNAse protections which are at least ten times more sensitive than primer extensions, were done on the same samples essentially as described by Melton et al., (1984) *Nucl Acids Res* 12:7035–7056. The data from these experiments are shown in FIG. 3. Transcripts with homology to the Gp2 cDNA are absent from leaf, root, petiole, stem and flower, but are present at low level in seed and peduncle, and at very high levels in developing fruit.

Example 4

Isolation of a Gene from Pepper Plants Encoding Gp2 Protein and Containing the Gp2 Promoter In order to isolate the genomic DNA region corresponding to the Gp2 gene, a genomic library was prepared from pepper DNA, and the Gp2 cDNA clone was used to screen the genomic library. The coding region from the cDNA was then aligned against the genomic region in order to identify the promoter region of the gene.

Pepper plants were grown in the greenhouse and nuclear DNA was isolated from young leaves as described in Dunsmuir, et al. (1983) *J. Mol. Appl. Genet.,* 2, 285–300. The DNA was partially digested with Sau3A followed by size fractionation on a glycerol gradient as described in Sambrook et al., (1989). DNA in the 15–20 kb range was cloned into the BamHI site of the lambda DASH II cloning vector (Stratagene, San Diego, Calif., USA) followed by in vitro packaging with Gigapack extracts (Stratagene) and plating in *E. coli* strain LE392. Six hundred thousand recombinant phage clones were screened with a Gp2 (pGP23) riboprobe and three independent phage which hybridized with the probe were isolated.

Figure 4:
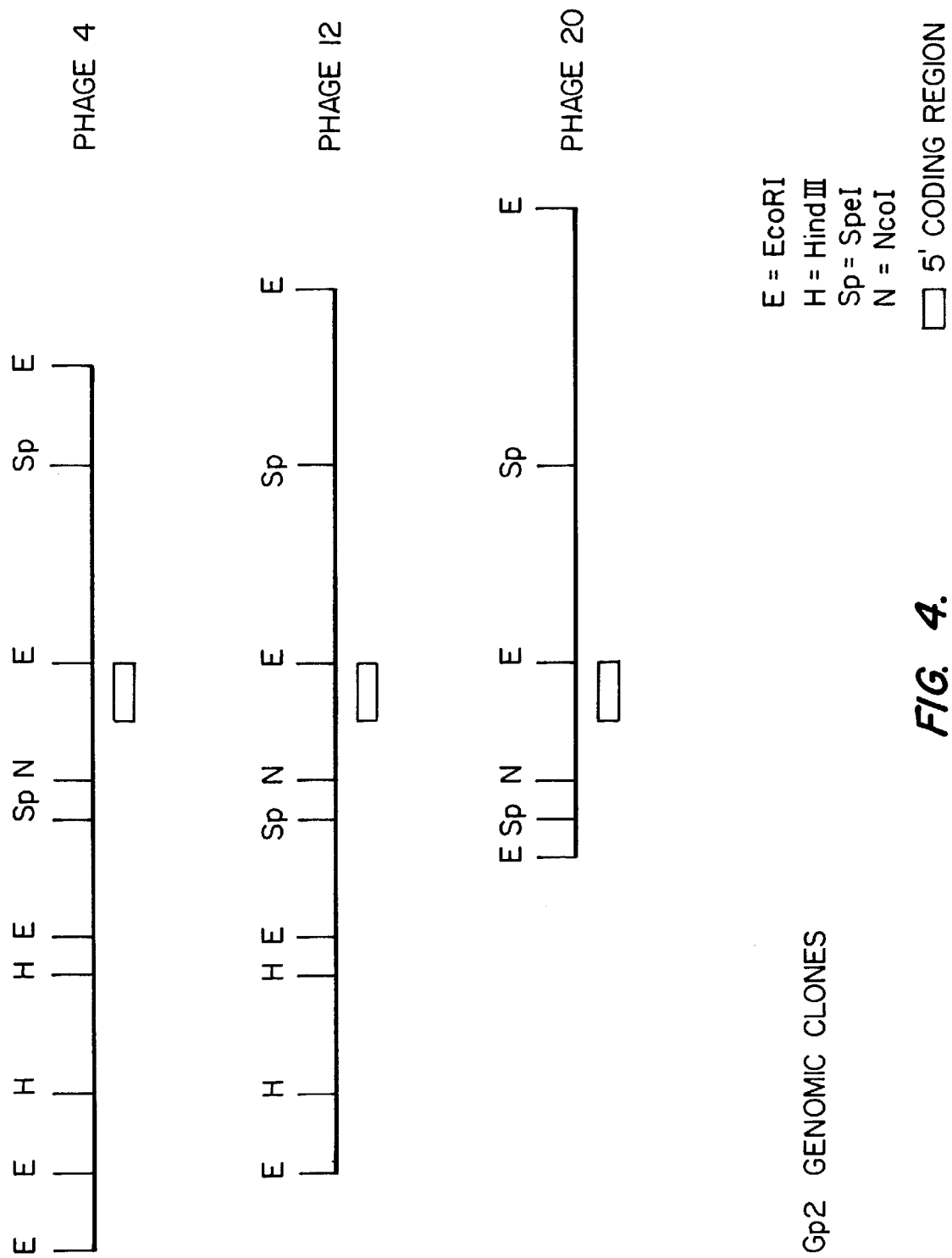
FIG. 4: Restriction maps of the phage 4, phage 12 and phage 20 Gp2 genomic clones obtained from *Capsicum annum* cv D2XYBA pepper plants. DNA prepared from the three genomic phage, #4, #12, and #20, were digested with EcoI, HindIII, SpeI, and NcoI and restriction maps were generated. The following abbreviations are used: E=EcoI, H=HindIII, Sp=SpeI, and N=NcoI.

DNA prepared from the three genomic phage (#4, #12, #20) that hybridized to the Gp2 cDNA were digested with EcoRI, HindIII, SpeI, and NcoI and restriction maps were generated. The restriction maps are shown in FIG. 4. The clones overlap and appear to be derived from a single genomic region. Hybridization of the Gp2 cDNA probe to the phage DNAs localized the Gp2 coding region as shown in FIG. 4 by a boxed area. An expression cassette was prepared using the 6.1 kb SpeI fragment from phage #4. This fragment, which included the Gp2 coding sequence and approximately 2.5 kb of 5' noncoding sequences and 2.0 kb of 3' noncoding sequences was subcloned into the SpeI site of BS(+) (Stratagene, San Diego, Calif., USA) to give plasmid PEP4-2.

Figure 5:
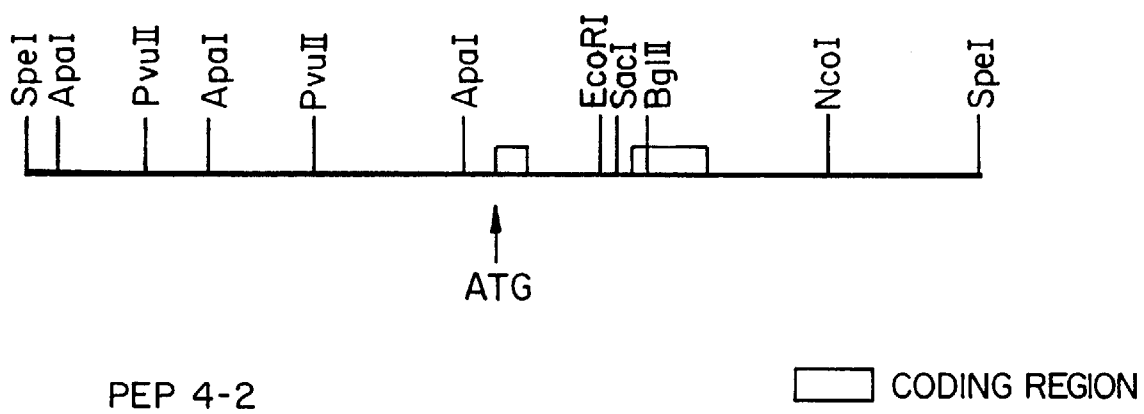
FIG. 5: Restriction map of Gp2 clone PEP4-2. DNA from clone PEP4-2 was digested with ApaI, NcoI, SacI, BglII and PvuII and a restriction map was generated. The coding region is the boxed region indicated on the restriction map.

The plasmid PEP4-2 consists of 6.1 kb of pepper genomic DNA. A more detailed restriction map was generated with the enzymes ApaI, NcoI, SacI, BglII and PvuII (see FIG. 5). Precise localization of the Gp2 gene coding region within this fragment was achieved by sequence analysis of regions on the genomic clone which hybridized to the cDNA and alignment of these sequences with the known Gp2 cDNA sequence. There was complete agreement between the sequences of the genomic region and the cDNA clone except for the presence of an intron in the genomic DNA. The regions sequenced corresponded to 111 bp of the 5' end of the cDNA, including 47 bp of untranslated sequences and 54 bp of coding region, and approximately 300 bp of the 3' untranslated region. These data indicated that the genomic region cloned in phage #4 is the genomic equivalent of the Gp2 cDNAs and that the Gp2 transcripts present in fruit derive from this gene. Hence the DNA from PEP4-2 was used for the promoter isolation and preparation of an expression cassette.

Example 5

Preparation of an Expression Cassette Containing a Short Form of the GP2 Promoter A short form of the Gp2 promoter was produced using a restriction fragment of the Gp2 promoter region obtained from the PEP4-2 clone. Subsequently, site directed mutagenesis was used in order to introduce a restriction site at the translation start codon for the Gp2 protein.

Figure 6:
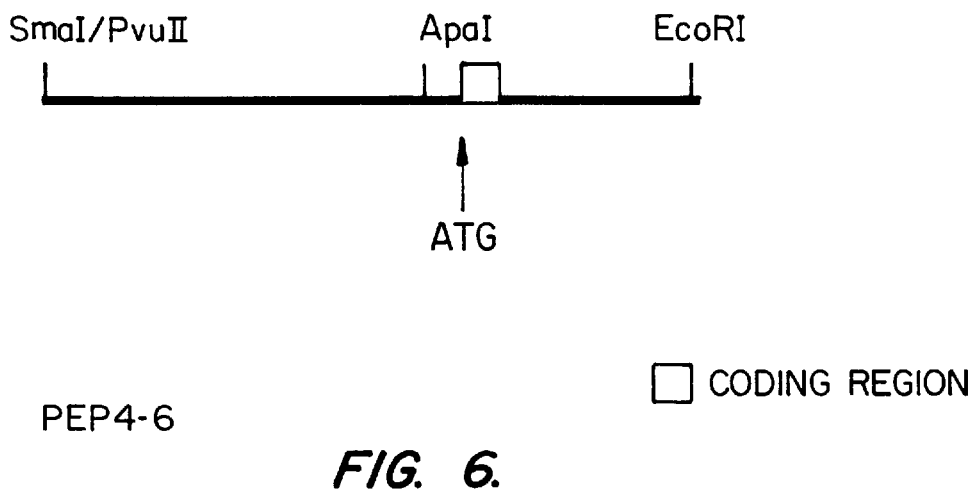
FIG. 6: Restriction map of Gp2 clone PEP4-6. The coding region is the boxed region indicated on the restriction map.

From the PEP4-2 clone, described in Example 4, herein, the 2.1 kb EcoRI-PvuII fragment (see FIG. 5), containing 1.2 kb of the 5' untranslated region and 900 bp of coding and intron sequences, was subcloned into the EcoRI-SmaI site of BS(−) vector (Stratagene) to give rise to plasmid PEP4-6 (FIG. 6). The 1.2 kb promoter region which is represented in this new clone called PEP4-6, corresponds to Gp2(short) promoter. Site directed mutagenesis was used to introduce a restriction site at the position of the translation start to facilitate fusions to this promoter. The sequences surrounding the translation start of the Gp2 coding region were mutagenized according to the method of Kunkel (1985) *Proc. Nat'l. Acad. Sci.* 82: 488–492 in order to introduce a NcoI site. The oligonucleotide which was used for this purpose is shown below:

5' GCCAG<u>CCATGG</u>TAATATTTTTGG 3'     (SEQ ID NO:6)

NcoI

The mutant clone PEP4-6mut was subsequently used as the source of a Gp2(short) promoter fragment.

The sequence of pepper genomic DNA in PEP4-6 clone was determined by the Sanger dideoxy method and is shown as SEQ ID NO:2. The promoter region of this sequence is shown as SEQ ID NO:2. The sequence of the PEP4-6 clone is identical to the sequence of the cDNA clone in the regions which they have in common, namely the transcription leader in the cDNA and the 5' end of the coding region up to where the intron interrupts the gene coding sequence (bases 1170 to 1295). The cDNA clone is identical to the sequence in the PEP4-2 clone throughout the entire coding region, and approximately 300 bp downstream of the stop codon.

Example 6

Production of a Vector Containing a Short Form of the Gp2 Promoter Operably Linked to the uidA Gene The short form of the Gp2 promoter produced in Example 5 was operably linked to the uidA gene, in order to examine the expression of DNA sequences linked to this form of the Gp2 promoter. The β-glucuronidase (uidA) reporter gene (GUS) was fused to the Gp2 (short) promoter by digestion of the PEP4-6mut clone with NcoI and HindIII and replacement of the Gp2 coding region with the NcoI-HindIII fragment containing the uidA coding region and nos terminator from the plasmid pJJ3411 (see Jones et al., (1992) *Transgenic Research* 1: 285–297). The newly created plasmid was called PEP4-6GUS.

To insert the promoter/uidA fusion gene into the binary vector pJJ2964 (Jones et al. (1992) supra) the plasmid PEP4-6GUS was digested with BamHI and HindIII and the DNA fragment containing the Gp2(short)/uidA/nos 3' fusion was gel purified followed by ligation into the BamHI-HindIII site of pJJ2964. The newly formed binary vector JJ2964/PEP4-6GUS was transferred by triparental mating with *E. coli* strain HB101/pRK2013 (Figurski and Helinski (1979) *Proc Natl Acad Sci* 76:1648–1652) into the *A. tumefaciens* strain LBA4404 (Hoekema et al., (1983) *Nature* 303: 179–180) which contains the virulence region of the Ti plasmid.

Example 7
Transformation of Plants With a Vector Containing a Short Form of the Gp2 Promoter Operably Linked to the uidA Gene 1) Preparation of an Agrobacterium Strain Carrying the pJJ2964/PEP4-6GUS Plasmid Fresh cultures of *A. tumefaciens* LBA 4404 harboring plasmid pAL4404 were grown at 28° C. for 24 h from a single colony in minimal A. *E. coli* HB101 containing the plasmid pRK2013 and *E. coli* HB101 containing pJJ2964/PEP4-6GUS prepared as described in Example 6 were grown for 6 hours in L broth. 0.5 ml of the *A. tumefaciens* culture were mixed on the same LB agar plate with 0.25 ml of HB101/pRK2013 and 0.25 ml of HB101 containing pJJ2964/PEP4-6GUS and the plates were incubated for 24 hours at 28° C. A loopful of bacteria from each plate was then resuspended in 1 ml minimal A and plated at $10^0$, $10^{-2}$ and $10^{-4}$ dilutions on LB plates containing 100 μg/ml rifampicin and 1 μg/ml tetracycline. After several days growth at 28° C., individual colonies were restreaked onto minimal A plates containing 1 μg/ml tetracycline. Subsequently the Agrobacterium strain which carried the pJJ2964/PEP4-6GUS plasmid was used in the transformation of tobacco and tomato.

2) Transformation of Tobacco Plants

All manipulations described below were carried out under sterile conditions. A culture of the Agrobacterium stain containing the requisite binary plasmid was grown for 24 hours in minimal A medium at 28° C. Leaf discs were punched from the leaves of SR1 Nicotiana tabacum plants grown under sterile conditions (Maliga et al. (1973) *Nature New Biol.* 244:29–30) using a cork borer with internal diameter 0.5 cm. The Agrobacterium cultures were diluted in MS/B5 0.1 to a final concentration of $5 \times 10^5$/ml. The leaf discs were dipped into the Agrobacterium suspension for 1 second each and then placed on co-cultivation plates, with 10 discs per plate. Co-cultivation plates were solid MS/B5 0.1/1.0 overlaid with a single, sterile Whatman #1, 7 cm filter disc. The leaf discs were co-cultivated with the Agrobacterium for 2 days at 28° C. The co-cultivation was terminated by washing the leaf discs in MS/B5 0.1/1.0 containing 500 μg/ml cefotaxime for 6 hours with one change of medium. The discs were then placed on solid MS/B5 0.1/1.0 containing 500 μg/ml cefotaxime and incubated for 3 days at 28° C. The discs were then transferred to selective medium: MS/B5 0.1/1.0 containing 500 μg/ml cefotaxime and 100 μg/ml kanamycin. The discs were cultured on this medium under high light flux with a 16 hour light, 8 hour dark regime at 26° C. After 2–3 weeks, kanamycin-resistant callus and subsequently kanamycin-resistant shoots begin to appear. When these were sufficiently large to handle with sterile forceps, they were transferred to rooting medium (MS 0.1/1.0 with no naphthalene acetic acid or 6-benzylaminopurine, containing 2 μm indole butyric acid) without selection, and allowed to form roots for 14 days. They were then excised and retransferred to rooting medium containing 100 μg/ml kanamycin. Plants that successfully developed roots on this medium were all transformants. They were then transferred to magenta boxes containing solid MS 0.1/1.0 without naphthalene acetic acid or 6-benzyl aminopyrine.

3) Transformation of Tomato Plants

All manipulations were carried out under sterile conditions. A culture of Agrobacterium LBA4404 containing the pJJ2964/PEP4-6GUS plasmid was grown for 24 hours in minimal A medium at 28° C. Explants were excised from the midsections of 7–8 day old cotyledons of sterilely grown *L. esculentum* seedlings on germination medium. The Agrobacterium culture was diluted in liquid 2% glucose-Oms to a final concentration of $5 \times 10^5$/ml.

The explants were submerged in the Agrobacterium suspension for 20–30 minutes and then placed on cocultivation plates for 2 days at 25° C. The cocultivation was terminated by washing the leaf discs in liquid 2% glucose-Oms for 2 hours. The explants were then placed on solid regeneration media and cultured under high light fluence with an 8 hour dark period at 25° C. After 10 days kanamycin resistant callus appeared and then small shoot buds by 3 weeks. At 5 weeks the healthy calli and shoots were transferred to fresh selection regeneration medium and within 2 weeks many transformed shoots emerged. The shoots were then excised and transferred to selective rooting medium. Plants that successfully developed shoots in this medium in 6–10 days were all transformants. These plants were then transferred to non-selective rooting medium for 2 weeks to check for residual Agrobacterium, then transplanted to soil.

Example 8
Measurement of uidA Gene Expression in Transformed Plants

An advantage of using the β-glucuronidase marker gene is that it is feasible to measure either RNA levels or enzyme activity in order to monitor promoter activity. In this example, GUS RNA levels were measured by the RNAse protection method in tomato plants. In addition, enzyme activity was measured using the substrate 4-methyl umbelliferyl glucuronide (MUG) in transformed tobacco plants.

RNAse protection and/or primer extensions were done to quantitate the level of RNA in the different tissues of the transgenic plants. A riboprobe containing approximately 90 bp of uidA coding sequence beginning at the ATG was used in the RNAse protection assays. As described by Melton et al., (1984), supra, 10 μg of total RNA isolated from transgenic tobacco leaf, stem and flower was hybridized to $^{32}P$ in vitro labeled RNA riboprobe. The hybrids were RNAse A/RNAse T1 treated and the digestion products (protected fragments) separated on an acrylamide gel. Six independent primary tobacco transformants were analyzed by RNAse protection and found to have similar uidA mRNA levels present in leaf, stem and flower. See Table 1 below. The positive control used in these experiments was a tobacco transformant carrying the CaMV35S:uidA construct, and the levels of mRNA expression measured in the leaf of this plant was ++.

For Tables 1, 2, 5A, 5B, 6, 8 below, the measurements are recorded on the following ascending 6-step scale (with approximately equal intervals between steps): -, (+), +, ++, +++, ++++, with the first step (dash) being not detected and the last step (quadruple plus) being highest level. Where a blank is shown, no measurement was made.

TABLE 1

Measurement of uidA mRNA levels in transgenic tobacco transformed with Gp2(short)/uidA

| Transformant | Leaf | Stem | Flower |
| --- | --- | --- | --- |
| Gp2.GUS-1 | +++ | +++ | +++ |
| -2 | +++ | +++ | +++ |
| -3 | +++ | +++ | +++ |
| -4 | +++ | +++ | +++ |
| -7 | +++ | +++ | +++ |
| -8 | +++ | +++ | +++ |

RNA levels were determined in RNAse protection experiments.

Six independent tomato transformants were found to have similar uidA mRNA levels in red (r) and green (g) fruit and leaf tissue (Table 2). Total RNA was isolated from a wider range of different tissues in three of the tomato transformants and analyzed by primer extension analysis (Dunsmuir et al., 1987) using a 20 bp oligonucleotide positioned 13 bp downstream of the translation start in the uidA gene. The sequence of the primer which was used is shown below:

5' GATTTCACGGGTTGGGGTTT 3'  (SEQ ID NO:7)

Using the primer extension assay uidA mRNA was detected in flower, petiole, stem, peduncle, calyx and seed (seed expression was seen in only one individual). The expression level of the introduced Gp2(short)/uidA gene was similar among the different tissues. See Table 2 below. The positive control plant used in these experiments was a tomato plant transformed with the CaMV35S:uidA construct, and the measured uidA RNA level in leaf was ++.

TABLE 2

Measurement of uidA mRNA levels in transgenic tomato transformed with Gp2 (short)/uidA

| Trans # | F-q. | F-r. | leaf | flow. | peti. | stem | ped. | caly. | seed | root |
|---|---|---|---|---|---|---|---|---|---|---|
| Gp2-204 | ++ | ++ | ++ | + | ++ | ++ | ++ | + | + | ++ |
| - 210 | + | ++ | ++ | ++ | ++ | ++ | ++ | ++ | ++ | ++ |
| - 305 | ++ | ++ | ++ | | | | | | | |
| - 308 | ++ | ++ | ++ | | | | | | | |
| - 310 | ++ | ++ | ++ | | | | | | | |
| - 321 | + | + | ++ | + | ++ | + | + | + | - | + |

RNA levels were determined by primer extension.

GUS assays were done on protein extracts from three of the PEP4-6GUS tobacco transformants essentially as described in Richardson et al., (1987) *EMBO* 6: 3903–3907. Extracts from leaf, pod, stem, seed, root and whole flower tissue were analyzed and GUS activity was detected in all tissues. The highest activity per mg total protein was found in the seed, followed by root and leaf, stem, flower and pod. The expression of GUS activity in the Gp2(short)/uidA transformants was similar to the levels observed in a transformant with a CaMV35S/uidA gene which is considered to be constitutively expressed. (See Table 3 below)

TABLE 3

Measurement of GUS activity in controls and transgenic tobacco plants transformed with the Gp2 (short)/uidA gene. (pmoles 4-methylumbelliferone/min/mg protein)

| Plant | Flower | Leaf | Stem | Seed | Pod | Root |
|---|---|---|---|---|---|---|
| Untrans. | 1.1 | 0.2 | 0.3 | 3.4 | 0.57 | 3.2 |
| Gp2s/uidA #1 | 1.1 | 763.7 | 60.0 | 265.1 | 1.57 | 935.2 |
| #2 | 2.2 | 935.9 | 324.4 | 3503.0 | 1.88 | 930.5 |
| #3 | 2.2 | 683.3 | 507.7 | 3225.7 | 1.88 | 911.6 |
| 35S/uidA | 6.7 | 391.6 | 102.7 | 3329.1 | 1.53 | 423.5 |

When the Gp2 (short) promoter is fused to the uidA gene, the levels of GUS mRNA or GUS activity are similar between different tissues within the transgenic plant. The data presented in tables 2 and 3 indicate that the Gp2 (short) promoter used in these experiments directs a constitutive pattern of expression in tomato and tobacco plants.

Example 9

Figure 7:
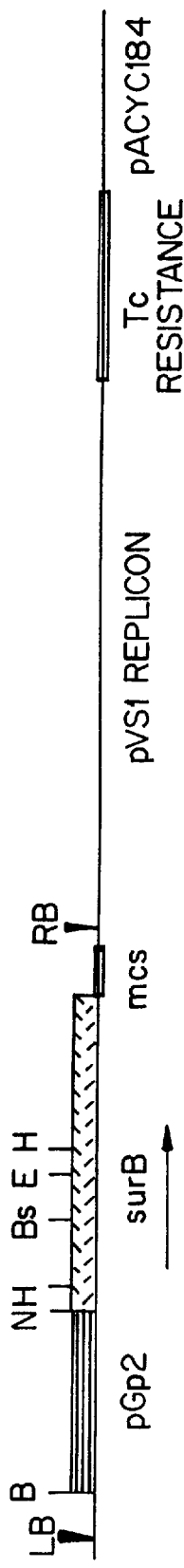
FIG. 7: Restriction maps of vectors WTT2132 and WTT2179. The following abbreviations are used: B=BamHI, Bs=BstEII, E=EcoRI, H=HindIII, N=NcoI, and mcs=molecular cloning site.
Figure 7:
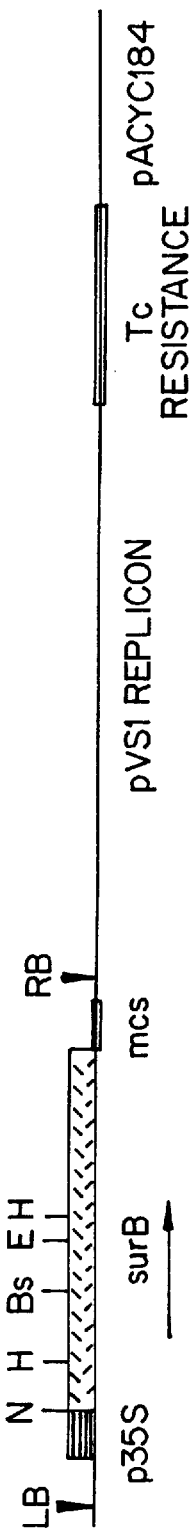

Transformation of Plants With a Vector Containing a Short Form of the Gp2 Promoter Operably Linked to the ALS Gene Data have also been obtained regarding the expression of the acetolactate synthase gene (SuRB or ALS) after fusion to the Gp2(short) promoter. The ALS gene which was used is a mutant form which confers resistance to the herbicide chlorsulfuron (see Lee et al., (1988) *EMBO J.* 7;1241–1248). WTT2132 (FIG. 7) is a binary vector containing the following components: the tetracycline resistance (tetR) gene, fragments containing the replicon from pACYC184 (Chang and Cohen (1978) *J. Bacteriol* 134: 1141–1156) and pVSI (Itoh et al., (1984) *Plasmid* 11: 206–220). In addition there is the 35SCab22L promoter (Harpster et al., (1988), *Molecular and Gen. Genetic,* 212:182–190) fused to the tobacco surB gene (Lee et al., (1988), supra), and the lacZa fragment of the B-galactosidase gene (Yanisch-Perron et al.,(1985) *Gene* 33: 103–119) located between the left and right T-DNA borders from the *A. tumefaciens* octopine Ti-plasmid (van den Elzen et al., (1985) *Plant Mol Biol* 5: 149–154). BglII linkers were added at the BamHI site in the PEP4-6GUS plasmid such that the Gp2 promoter (short) could be isolated on a 1.2 kb BglII-NcoI fragment. This fragment was substituted for the BglII-NcoI fragment which carries the 35SCab22L promoter in WTT2132, forming the binary vector WTT2179 (FIG. 7). This plasmid was subsequently transferred to *A. tumefaciens* LBA4404 (Hoekema et al. 1983, supra) by triparental mating.

1) Transformation of Tomato Plants

Tomato plants were transformed with *A. tumefaciens* containing the WTT2179 plasmid as described in Example 7, above.

2) Transformation of Pepper Plants

The protocol for the transformation of pepper is as described in Example 3 of U.S. Pat. No. 5,262,316, except that the explants were not washed after cocultivation, initiation medium was 10BIcscf and maturation medium was B4cs. Shoots were rooted by transfer to Sorbarod plugs (Baumgartnen Papiers SA, Switzerland) soaked in liquid YRM (see below). Shoots were confirmed for transformation using the recallusing assay on OMSG plus 0.5 mg/l kinetin and 0.5 mg/l 2,4-D, and by PCR using the oligonucleotides DEALS1 and DEALS2 as described for pea below.

| YRM | |
|---|---|
| N6 salts and iron[1] | 1/2X |
| Thiamine | 1 mg/l |
| Sucrose | 30 g/l |
| IAA* | 2 mg/l |
| pH | 5.7 |

*Add IAA after autoclaving
[1]See Chu et al., (1975) Scientia Sinica 19:659–668

3) Transformation Frequencies for Tomato and Pepper

The relative transformation frequencies for both tomato and pepper transformation were compared for the Gp2 (short)/ALS selectable marker and the CaMV35S/ALS selectable marker. The transformation frequencies listed by species in Table 4 below.

TABLE 4

A. TOMATO
Transformation frequency (#rooted transformants/# explants) and escape frequency (unrooted shoot #/total # shoots) comparison between Gp2 (short)/SurB or CaMV35S/SuRB selectable markers

| Binary Vector | Selectable Marker | Transformation Frequency | Escape Frequency |
|---|---|---|---|
| WTT2084 | 35S/ALS | 28/160 | 31/60 |
| WTT2132 | 35S/ALS | 19/160 | 27/46 |
| WTT2179 | Gp2(s)/ALS | 21/160 | 15/36 |

B. PEPPER
Transformation frequency (190 rooted transformants/# explants) and % explants shooting (# shoots/# cocultivated) comparison between Gp2(short)/SurB or CaMV35S/SuRB selectable markers

| Binary Vector | Selectable Marker | explants shooting | Transform. Frequency |
|---|---|---|---|
| 2104/Cld10 | 35S/ALS | 409/7900 | 13/7900 (.38%) |
| WTT2132 | 35S/ALS | 140/1480 | 14/1480 (.95%) |
| WTT2179 | Gp2(s)/ALS | 89/1880 | 3/1880 (.37%) |

Example 10
Measurement of ALS Gene Expression in Transformed Plants

ALS gene expression was measured in the transformed tomato and pepper plants produced in Example 9. ALS RNA levels were measured in both leaf and fruit tissue. RNAse protection analysis (Melton et al., 1984, Supra) with a riboprobe containing 90 bp of the 5' coding sequence of the SurB gene (Lee et al., 1988, supra) was used to quantitate the level of ALS RNA in the transgenic tomato and pepper plants. 7 tomato plants and 2 pepper plants transformed with WTT2179 binary vectors were analyzed and found to have ALS RNA in both leaf and fruit tissue. These data illustrate that Gp2(short) functions to direct expression of the SuRB gene in multiple tissues of transgenic tomato and pepper. These data are also consistent with that observed for the uidA gene fused to the Gp2(short) promoter. See Table 5, below. The positive control plants used in these experiments were tomato or (pepper) plants transformed with CaMV35S:ALS, where the measured ALS mRNA level in leaf was ++++.

TABLE 5A

Measurement of ALS RNA expression in tomato plants transformed with Gp2(short) -ALS: RNAse protection analysis

| Transformant # | Young leaf | Old leaf | Red fruit |
|---|---|---|---|
| Al101 | + | + | ++ |
| Al102 | + | + | ++ |
| Al103 | + | ++ | ++ |
| Al104 | − | + | ++ |
| Al202 | ++ | ++ | +++ |
| Al203 | + | +++ | +++ |
| Al204 | +++ | + | + |

TABLE 5B

Measurement of ALS RNA expression in pepper transformed with Gp2(short) -ALS or CaMV35S-ALS: RNAse protection with ALS probe

| Transformant # | leaf | green fruit | red fruit |
|---|---|---|---|
| 1Ac01a | ++ | +++ | ++ |
| 1Ac02a | +++ | +++ | +++ |
| 1Ac03a CaMV35S | ++++ | ++++ | ++++ |
| 1Ac04a CaMV35S | + | +++ | ++ |

The Gp2(short) promoter has been used to drive the ALS gene as a selectable marker and found to perform like the CaMV35S promoter in this regard. RNAse protection has been used to directly compare the relative levels of ALS expression of the CaMV35S promoter and the Gp2(short) promoter fusions in transgenic tomato and pepper tissue. The relative transformation frequencies achieved using the CaMV35S promoter and the Gp2(short) promoter fused to ALS have been quantitated as a measure of relative strength of the two promoters. As shown in Table 5B, the strengths of the two promoters is similar.

Example 11
Transformation of Tomato Plants With a Vector Containing a Short Form of the Gp2 Promoter Operably Linked to the AccS Gene Tomato plants were also transformed with a vector containing a short form of the Gp2 promoter fused to an AccS gene fragment. The AccS gene fragment encodes ACC synthase.

Figure 8:
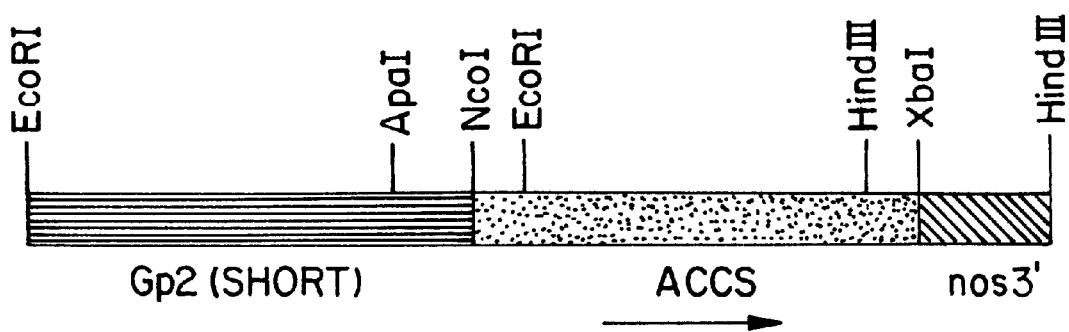
FIG. 8: Restriction map of plasmid PEP4-6AccS.

The plasmid 35SAccS contains the 35S Cab22L promoter (Harpster et al., 1988, supra) fused to a fragment of the fruit specific ACC synthase gene, Acc2 (see Rottman et al., (1991) *J. Mol. Biol.* 222: 937–961). The PCR reaction with oligonucleotides located 160 bp downstream from the translation start and 210 bp upstream from the stop codon was used to generate a 5' and 3' truncated version of the gene. The PCR fragment was ligated, in frame, to the 35SCab22L promoter and the nos3' terminator. The plasmids 35SACCS and PEP4-6GUS were both digested with NcoI and XbaI then the 1.1 kb AccS fragment from 35SACCS and the 4.3 kb fragment from PEP4-6GUS containing the BS(+) vector, the Gp2(short) promoter and the nos3' end were gel purified, ligated together and transformed into *E. coli* strain MV1193 to form PEP4-6AccS (FIG. 8).

PEP4-6AccS was digested with BamHI and ClaI and the ends made flush with Klenow enzyme. The fragment was gel purified and ligated into the SmaI site of both WTT2179 or WTT2132 (see above) to form WTT2179/PEP4-6AccS and WTT2132/PEP4-6AccS. Orientation of the PEP4-6AccS fragment relative to the right border was determined by restriction digest. Subsequent transfer of the plasmid to *A. tumefaciens* strain LBA4404 (Hoekema et al., 1983, supra) was by triparental mating.

Tomato plants were transformed with *A. tumefaciens* LBA4404 containing either the WTT2179/PEP4-6 ACCS or WTT2132 PEP4-6 ACCS plasmids as described in Example 7, above.

Example 12
Measurement of AccS Gene Expression in Transformed Tomato Plants

AccS RNA levels were measured in leaves of 13 transgenic tomato plants produced in Example 11, by RNAse protection assays. A riboprobe protection fragment was prepared from 35SAcc2FL which consists of a 35SCab22L promoter (Harpster et al., 1988, supra) fused to a full length PCR generated Acc2 (Rottman et al., 1991, supra) coding sequence and the nos3' end. The XhoI-EcoRI fragment which carried the Cab22L and the first 285 base pairs of the Acc2 coding sequence was cloned into the SalI-EcoRI site of BS(+) (Stratagene San Diego, Calif., USA) and used as the probe in protection experiments. AccS transcripts were detected in leaf tissue in 7 of 11 of the WTT2179/PEP4-6AccS transformants analyzed and in 2 out of 2 WTT2132/PEP4-6AccS transformants (data not shown). This analysis indicated that the Gp2(short) promoter directed expression of AccS in leaves of tomato.

Figure 9:
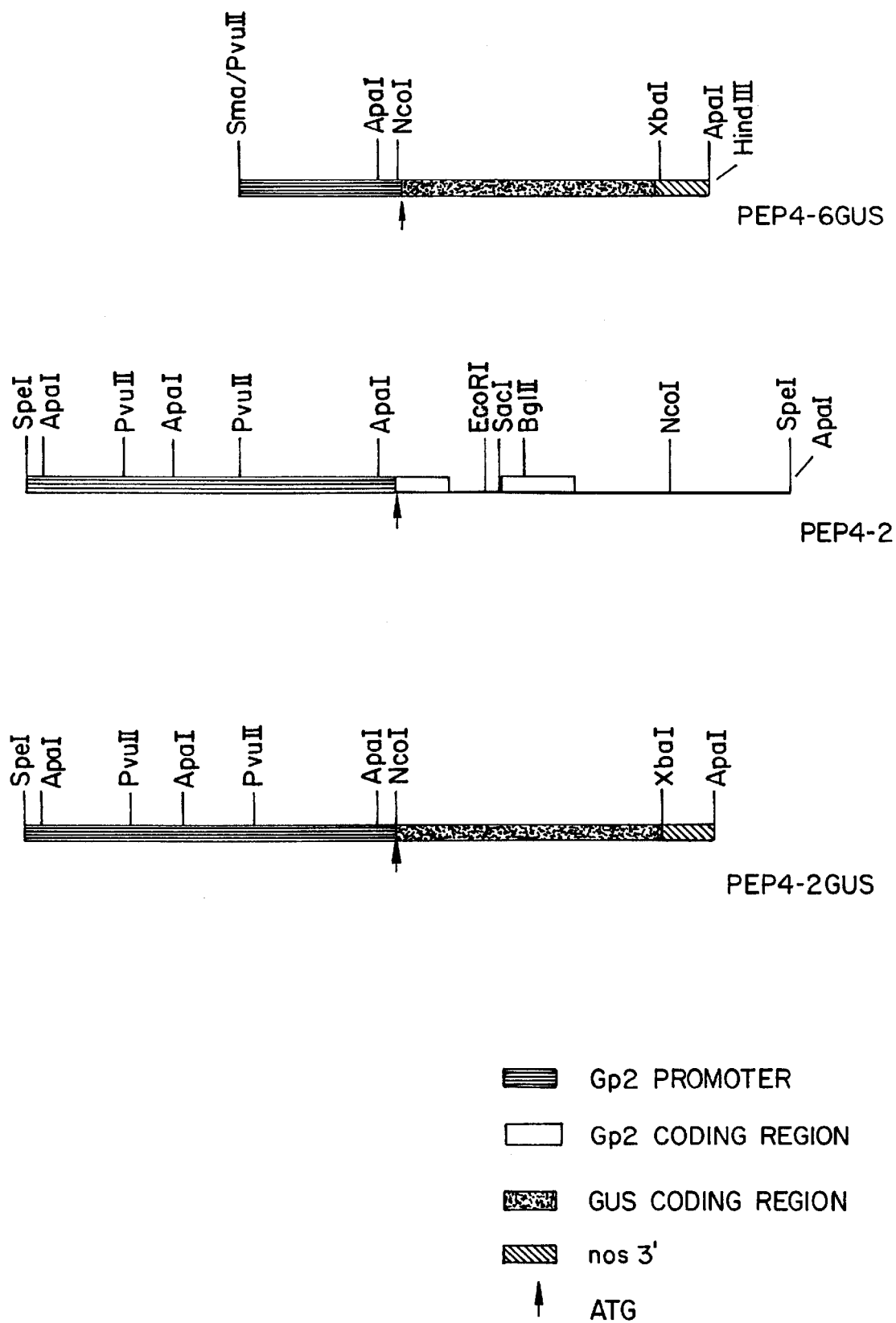
FIG. 9: Restriction map diagrams of plasmids PEP4-6GUS, PEP4-2, and PEP4-2GUS. The region indicated in black is the Gp2 promoter; the region indicated in white is the Gp2 coding region; the hatched region is the GUS coding region; the striped region is the nos 3' region; and the ATG start codon is indicated with an arrow.

Example 13
Preparation of a Vector Containing a Long Form of the Gp2 Promoter Fused to the uidA Gene A long form of the Gp2 promoter was prepared by fusing an additional 1.6 kb from the Gp2 promoter to a short form of the Gp2 promoter. The plasmid PEP4-2 (FIG. 9) was partially digested with ApaI and the 5.6 kb fragment containing the BS(+) vector and 2.6 kb of the 5' untranslated region (promoter) upstream of the ApaI site that is closest to the ATG, was then ligated to the ApaI fragment from PEP4-6GUS which includes the 5' untranslated region between the ApaI site and the NcoI site of Gp2(short) promoter fused to the uidA coding region and the nos3'. This newly formed plasmid, PEP4-2GUS (FIG. 9) was digested with SpeI, the ends filled in with Klenow, followed by digestion with HindIII. The 4.6 kb fragment carrying the Gp2(long) promoter fused to the uidA gene and nos3' end was gel purified and cloned into the HpaI-HindIII sites of JJ2964 (cited above) to create JJ2964/PEP4-2GUS.

Plasmid PEP4-2GUS was deposited according to the terms of the Budapest Treaty with the American Type Culture Collection (ATCC) of 12301 Parklawn Dr., Rockville, Md. USA on Jun. 15, 1994 and assigned Accession No.: 75816. If the plasmid PEP4-2GUS is digested with NcoI and PvuII, the 1.2 kb fragment which is released can be used as a constitutive promoter. The 1.2 kb fragment corresponds to SEQ ID NO:4. If the plasmid PEP4-2GUS is digested with NcoI and SpeI, the 2.8 kb fragment which is released can be used as a tissue-specific promoter.

A Gp2(long) promoter fused to the uidA gene and the Gp2 3' end was made by first introducing a XbaI site 17 bp downstream of the Gp2 stop codon by site directed mutagenesis (Kunkel, 1985) with a 18 bp oligonucleotide:

5' GAAAGTCTAGATGGATATAG 3'. (SEQ ID NO:8)
XbaI

The XbaI-HindIII fragment from this clone, PEP4-2Xbamut, which carried the Gp2 3' end was cloned into the partially digested XbaI-HindIII complete site of PEP4-2GUS to form PEP4-2GUS3'. To clone this fusion into the binary vector JJ2964, the plasmid PEP4-2GUS3' was digested with SacI and the ends filled in using T4 Polymerase. The DNA was then digested with HindIII. The fragment containing the Gp2(long) promoter fused to the uidA gene and Gp2 3' was ligated into JJ2964 at the HpaI-HindIII site forming the plasmid pJJ2964/PEP4-2GUS3' which was transformed into E. coli strain JM83. Both binary vectors JJ2964/PEP4-2GUS and JJ2964/PEP4-2GUS3' were transferred into A. tumefaciens LBA4404 (Hoekema, (1985, supra) by triparental mating.

Example 14
Transformation of Tomato Plants With a Vector Containing a Long Form of the Gp2 Promoter Fused to the uidA Gene Tomato plants were transformed with A. tumefaciens LBA4404 containing either the JJ2964/PEP4-2 GUS or JJ2964/PEP-2GUS3' plasmids, as described in Example 7, above.

Example 15
Measurement of uidA Gene Expression in Transformed Plants uidA mRNA levels were measured in 15 independent tomato transformants which carry either the Gp2(long)/uidA/nos3' gene (9 plants) or the Gp2(long)/uidA/Gp2-3' gene (6 plants). In all but one of these plants the levels of uidA MRNA is significantly higher in red (r) fruit than in leaves indicating that the long version of the Gp2 promoter directs tissue specific expression compared with the short version which directs constitutive expression. See Table 6, below. The positive control plants used in these experiments were tomatoes transformed with the CaMV35S:uidA construct, where the uidA RNA level in leaf was ++.

TABLE 6

Measurement of uidA mRNA levels in transgenic tomato transformed with Gp2(long)/uidA

| Transformant | Fruit-r | Leaf |
| --- | --- | --- |
| 4.2uidA-7201 | (+) | – |
| -7202 | ++ | (+) |
| -7205 | ++ | – |
| -7207 | ++ | – |
| -7210 | (+) | – |
| -7211 | – | – |
| -7218 | (+) | (+) |
| -7220 | ++ | – |
| 4.2uidA. 3'-12101 | +++ | – |
| -12103 | + | – |
| -12106 | ++ | – |
| -12107 | ++ | ++ |
| -12111 | +++ | – |
| -12112 | ++ | (+) |

GUS activity was also measured as described in Richardson et al., (1987, supra). Tissue from leaf, stem, root, flower, seed, and green (g) and pink (p) fruit was assayed in 3 transgenic plants transformed with 2964/PEP4-2GUS and 3 with JJ2964/PEP4-6GUS3'. Three additional JJ2964/PEP4-6GUS3' transformants were analyzed for activity in leaf and pink fruit only. Activity was detectable in all tissues in JJ2964/PEP4-2GUS transformants with the highest level in pink fruit followed by stem, root and green fruit, flower, seed and leaf. The JJ2964/PEP4-2GUS3' transformants had the same profile except that root had higher activity than green fruit and stem. In general, activity with the Gp2 3' end was lower than with the nos3' end. See Table 7 below.

TABLE 7

Measurement of GUS activity in transgenic tomato plants transformed with Gp2(long)/uidA gene (pmoles) 4-methylumbelliferone/min/mg protein).

| Trans. # | leaf | stem | root | flower | fruit-g | fruit-p | seed |
| --- | --- | --- | --- | --- | --- | --- | --- |
| -7202 | 25 | 2170 | 1807 | 176 | 569 | 3569 | 44 |
| -7206 | 17 | 1406 | 449 | 16 | 702 | 3746 | 36 |
| -7220 | 101 | 831 | 310 | 39 | 1395 | 5938 | 20 |
| -12101 | 21 | 186 | 1276 | 5 | 474 | 4328 | 73 |
| -12106 | 6 | 411 | 1937 | 7 | 656 | 2195 | 73 |
| -12111 | 1 | 5 | 241 | 1 | 48 | 1491 | 18 |
| -12108 | 40 | | | | | 1607 | |
| -12110 | 55 | | | | | 3311 | |
| -12113 | 1 | | | | | 238 | |
| no uidA | 1 | 1 | 1 | 1 | 5 | 7 | <1 |
| 35S/uidA | 537 | nd | nd | nd | nd | 5388 | 241 |

The above data illustrate that the Gp2(long) promoter directed significantly higher levels of expression of the uidA gene in pink fruit than in other tissues. Furthermore, the Gp2(long) promoter directs a different pattern of expression from the CaMV35S promoter.

Two different forms of a Gp2(long) promoter:uidA gene fusions have been compared. In one form, the nos terminator is used and in the other the Gp2 gene 3' region is used. Significant differences between the performance of these constructions in transgenic tomatoes have not been seen. Both forms direct much higher levels of expression in fruit than in leaves.

Example 16
Preparation of a Vector Containing a Long Form of the Gp2 Promoter Fused to the Cell Gene The pepper cell gene was isolated by screening a red pepper pericarp cDNA library (prepared in the lambda gt10 vector) with two different degenerate oligonucleotides which had been designed to correspond to a conserved 5' and 3' region within the published coding sequences for the avocado mesocarp and the bean abscission layer cDNAs. The sequences of these oligonucleotides are given below:

Oligo #1 5' TTA/GTCICCIGCA/GTCA/GTAA/GTAICCICC 3' (SEQ ID NO:9)
Oligo #2 5' TCCATA/GTCT/CTCIGGICGT/CTCCCAA/GCA 3' (SEQ ID NO:10)

At least twenty independent cDNA clones were isolated using this screening method and each of these was characterized by restriction enzyme analysis and also direct sequence analysis. Based upon this characterization, all such cDNA clones were determined to have derived from the transcription of a single gene, cell. In order to prepare the cell coding region for reintroduction and expression in plants, the coding region was modified by the addition of restriction enzyme cleavage sites at the translation start and adjacent to the translation stop. These sites allowed for the simple excision of the coding region from the cDNA clone and the subsequent fusion of the cell coding region to appropriate transcriptional control regions. Specifically an NcoI site was introduced at the translation start using oligonucleotide site directed mutagenesis with the following oligonucleotide:

Oligo #3 5' ATATATATAACCATGGCTTG 3' (SEQ ID NO:11)

NcoI

Then a Bgl II site was introduced adjacent to the translation stop using the oligonucleotide:

Oligo#4 5' AAATTGAAGATCTATAGTC 3' (SEQ ID NO:12)

BglII

Figure 10:
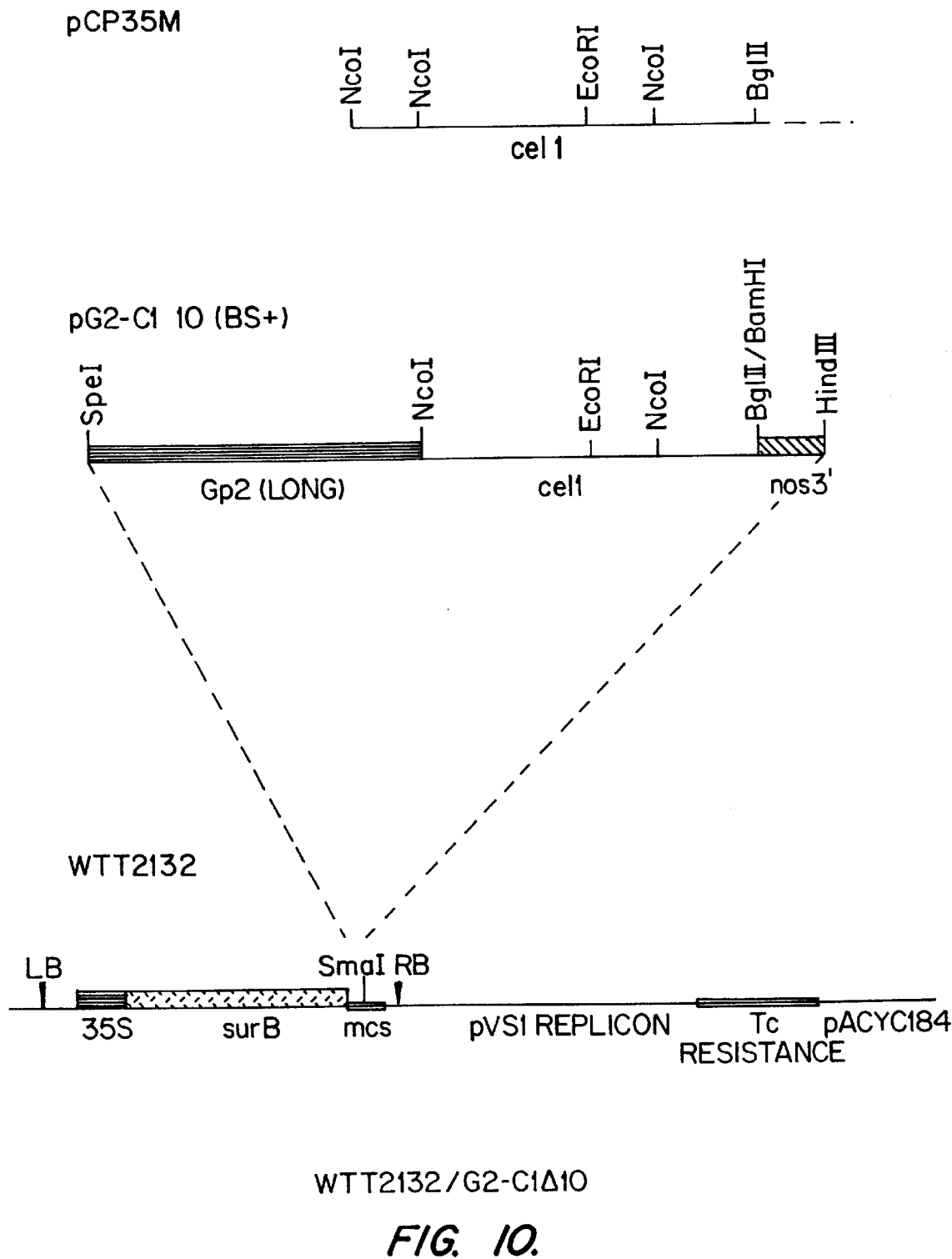
FIG. 10: Diagram showing the construction of plasmid pG2-C1Δ10 from pCP35M. The abbreviation "mcs" indicates the molecular cloning site in WTT2132.

The resultant plasmid was designated pCP35M (FIG. 10). A 5' deletion of the cell coding region was isolated from the plasmid pCP35M by partial digestion with NcoI and complete digestion with BglII. This deletion of 240 bases results in a coding region which specifies a protein which is missing 80 amino acids at the NH$_2$ terminal. This fragment was then inserted into the plasmid PEP4-2GUS which had been digested with NcoI and BamHl. The resulting plasmid, pG2-C1Δ10, was composed of a deleted form of the cell coding region fused to the Gp2(long) promoter at the 5' end, and the nos terminator at the 3' end (FIG. 10).

The deleted cell coding region flanked by the Gp2(long) promoter and the nos terminator was isolated after BglII and HindIII digestion of the plasmid pG2-C1Δ10 followed by the generation of blunt termini with Klenow enzyme, then inserted into the binary vector pWTT2132 which had been digested with SmaI. The resulting plasmid WTT2132/G2-C1Δ10 carried the cell gene with the Gp2(long) promoter and nos terminator adjacent to the ALS gene selectable marker (CaMV35S/SuRB) for plant cell transformation and between the left and right borders of the T-DNA which directs insertion into the plant genome during transformation (FIG. 10).

Example 17
Transformation of Pepper Plants With a Vector Containing a Long Form of the Gp2 Promoter Fused to the Cell Gene Pepper plants were transformed with A. tumefaciens containing the WTT2134 G2-C1 delta 10 plasmids, as described in Example 9, above.

Example 18
Measurement of Cell Gene Expression in Transformed Pepper Plants

Expression of the introduced cell gene was measured by direct quantitation of mRNA levels using the RNAse protection method. A probe fragment (which encompassed 330 bases of the pepper cell coding region) was prepared from pCP35-6L, which is a subclone from the pcell gene. This probe detected the introduced gene as a 260 base pair fragment and the endogenous gene as a 300 base fragment. Four independent transformants which express the cell transgene have been characterized (See Table 8 below).

TABLE 8

Measurement of cell mRNA levels in transgenic pepper plants transformed with Gp2(long)-cel1 measured by RNAse protection

| Transformant # | Transgene | | Endogenous | |
|---|---|---|---|---|
| | Leaf | Fruit | Leaf | Fruit |
| 1C01a | + | +++ | − | +++ |
| 1C07a | − | ++ | − | +++ |
| 1C13a | +++ | − | − | +++ |
| 1C20b | − | ++ | − | +++ |

In three of the transformants the level of the cell MRNA is much higher in fruit tissue than in leaf tissue. This is in contrast to the situation for CaMV35S/cell transformants. We evaluated CaMV35S/cell transformants in 6 plants and found similar levels of cell RNA in both leaf and fruit tissue (data not shown).

Overall, the Examples demonstrate that the Gp2 promoter is effective in both its short form (constitutive) and long form (tissue-specific) for controlling expression of a variety of genes (GUS, ALS, ACC synthase, Cell) in various plant species (tobacco, tomato, pepper).

Example 19
Fungal Antibiotic Properties of Gp2 Protein
1) Plate Assay

Defensins are a family of small, cysteine-rich, basic, antimicrobial plant proteins (Epple, P., et al., *FEBS Lett.* 400: 168–172 (1997). Gp2 proteins (see, e.g. SEQ ID NOS:1 and 2) are pepper defensins that are members of the defensin family based on sequence characteristics and anti-microbial activity. Reference to "defensin" indicates a defensin protein or an extract that contains defensins and exhibits defensin activity.

A petri plate method was used to score fungal antibiosis of plant intracellular fluid (IF) extracts. Agar plugs of actively growing fungal cultures of *Verticillium dalhae, Fusarium oxysporum* fsp. *lycopersici* Race 1, *Rhizoctonia solani, Botrytis cinerea,* and *Phytophthora infestans* (grown on Rye Seed Agar) were placed onto Malt Glucose Agar (MGA) supplemented without or with 5 mg or 500 mg/L of NaCl. IF extracts were prepared from red pepper pericarp. The pepper line VegiSweet 300 (VS300) was used. After 24 hr of fungal growth, fungal agar plugs and IF extracts were placed on a MGA plate. The agar plugs and the IF extracts were placed 25 mm apart. Three different concentrations of IF protein extracts were used for this assay: 10, 20, and 50 µg. Fungal growth was monitored over time by measuring mycelial growth. Three controls were used: IF from green pepper pericarp, IF buffer alone, and H$_2$O. This experiment was repeated several times with *Fusarium oxysporum* fsp. *lycopersici* Race 1.

In general, Fusarium was the most sensitive of the pathogens tested. Mycelial growth during the first 5 days was inhibited by 20 to 30% compared to the growth in controls. After approximately 5 days, the fungal cultures grew over the defensin treatments. The mycelial growth inhibition was slightly less at the higher NaCl concentration of 500 mg/L. Phytophthora, Rhizoctonia and Botrytis were only sensitive during the first two days of growth. Growth inhibition was approximately 5 to 10% of the controls and after day 2, growth was comparable to the controls. Although Verticillium grew so slowly on MGA that it was difficult to score, no inhibition was observed.

2) Microtiter Plate Assays

Another method was also used to monitor fungal antibiosis. The protocol for the assay is described in Terras et al., *J. Biol Chem.* 267:15310–309 (1992) and involves monitoring fungal growth in broth using a 96-well microtiter plate. IF fractions from pepper pericarp were taken, concentrated on a Centricon membrane (number 10) to remove components of the IF extraction buffer, and washed with a 0.1 M TRIS buffer pH 7.5. A fungal spores suspension (final concentration: approximately 1×10$^3$ spores/ml) or bacteria (final concentration: approximately 1×10$^5$ cells/ml) was added to ½ strength Potato Dextrose Broth (PDB) supplemented with or without 2.5 mM CaCl$_2$ and 50 mM KCl. In some experiments a minimal media was used instead of ½ PDB. Ten micrograms of protein from pepper pericarp IF extracts were then added and the optical density measured at 492 nm was monitored over 2–3 days. The final volume of each well was 100 µl with 3 replications per treatment. Table 9 lists the pathogens screened and the optical density values at 24 and 48 hr. Optical density values followed by an asterisk were significantly different than the control. The control treatment was the pathogen growing in medium alone.

After IF fractions were collected, a quantity of protein (25 to 50 µg/total) was separated on 15% tricine-PAGE allowing for an approximation of the Gp2 protein present in the IF samples. Analysis of variance was used to analyze the data and the Duncan's test was used for mean comparisons. Determination of protein concentration allowed for equal application samples.

Mycelial growth of Fusarium, Alternaria and Verticillium was significantly inhibited by the Gp2 in ½ PDB without salt. In the media supplemented with Ca$^{2+}$ and K$^+$, however, significant growth inhibition was only recorded for Verticillium at 48 hrs (Table 9). Mycelial growth of Phytophthora and Botrytis was not affected by the pepper defensin. This observation was different from the earlier experiment in which inhibition was observed (Example 19 plate assay). In those experiments, however, a non-washed IF protein extract was used and components within the extraction buffer could have contributed to the inhibition. Growth by Clavibacter was significantly inhibited with or without salts. Erwinia was inhibited in ½ PDB without salts. No growth inhibition of Erwinia was recorded in minimal media.

TABLE 9

In vitro growth inhibition by Gp2 against selected plant pathogens

| Pathogen | Media | Time | without salts | with salts |
|---|---|---|---|---|
| *Fusarium* | ½PDB | 24 | .015* | .024 |
| *oxysporum* fsp. | | 48 | .059* | .282 |
| *lycopersici* | | | | |
| Race 1 | | | | |
| *Alternaria* | ½PDB | 24 | .001* | .004 |
| *alternata* fsp. | | 48 | .013* | .386 |
| *lycopersic* | | | | |
| F310 | | | | |
| *Botrytis* | ½PDB | 24 | .017 | .074 |
| *cinerea* | | 48 | .020 | .328 |
| *Phytophthora* | Rye | 24 | .073 | na |
| *infestans* | seed | 48 | .245 | na |
| | broth | | | |
| *Verticillium* | ½PDB | 24 | .001 | .001 |
| *dahliae* Race 1 | | 48 | .001* | .042* |
| *Clavibacter* | ½PDB | 24 | .001* | .002* |
| *michiganensis* | | 48 | .001* | .048* |
| *Pseudomonas* | ½PDB | 24 | .218 | .246 |
| *syringae* pv | | 48 | .233 | .313 |
| *tomato* Race 0 | | | | |
| *Xanthomonas* | ½PDB | 24 | .007* | .033 |
| *cainpestris* pv. | | 48 | .101 | .145 |
| *vesicatoria* | | | | |
| *Erwinia* | ½PDB | 24 | .103* | na |
| *carotovora* 301 | | 48 | .261* | na |
| *Erwinia* | minimal | 24 | .186 | .185 |
| *carotovora* 301 | | 48 | .259 | .245 |

Optical density values followed by an asterisk were significantly different than the control. The control treatment was the pathogen growing in medium alone.

Example 20

Analysis of Transgenic Tomatoes Expressing Gp2 Protein

1) Northern and Western Analysis

The gene encoding a Gp2 protein (see, e.g., SEQ ID NO:1) was subcloned under the control of the CaMV 35S promoter and chlorosulfuron (pGrp2-SurB) was used as a selectable marker. Five lines of DNAP 92550 and 32 lines of Fireball tomato plants were selected for greenhouse evaluations. At approximately 4–5 weeks after transplanting from tissue culture, when the plants were at fruit set, all primary transformants were analyzed by northern blot analysis. IF preparations were made from leaves and western blot analysis was used to measure the protein levels of Gp2 protein. Antibody was obtained from R. Schantz. The antibody is described in Meyrs, et al., *Plant Physiol.* 112:615–622 (1996). The antibody was raised using a synthetic peptide subsequence corresponding to a selected amino acid sequence encoded by the JI-1 cDNA. The western blot analysis of pepper IF extracts from VS300 and Red MiniBell revealed a protein corresponding to the approximate size of Gp2 protein. Protein from these pepper cultivars were used as controls. Plants that showed both moderate to high mRNA and protein levels were saved. There was a general correlation between results from the northern blot and western blot analysis (Table 10). A set of moderate to very high expressing lines covered in Table 10 were further assayed for fruit size and fruit set (Table 11). F92550 and Fireball are controls in Table 11. Fruit size and fruit set ratings in Table 11 are defined as follows: 1=very small or low to 5=very large or high, respectively. Line F92550 is the parent background for the F38-lines and Fireball is the parent background for the G38-lines.

TABLE 10

Screening of 37 primary transformants in Fireball
and DNAP 92550: summary of Gp2 expressing tomato lines
(p35S-Gp2; pGp2-AL)

| Analysis | Relative amount of expression | | | | |
|---|---|---|---|---|---|
|  | nulls | low | moderate | high | very high |
| Northern | 7 (19%) | 3 (8%) | 18 (49%) | 7 (19%) | 2 (5%) |
| Western | 7 (19%) | 9 (24%) | 10 (27%) | 10 (27%) | 1 (3%) |

TABLE 11

Comparison of selected tomato lines expressing Gp2
protein for RNA, proteins expression, fruit size and set
Gp2 Expression Profile

| Lines | Northern Assay | Western analysis | Fruit Size | Fruit Set |
|---|---|---|---|---|
| F38005 | Very high | Very high | 4 | 3 |
| F92550 | 0 | 0 | 4 | 3 |
| G38003 | High | High | 3 | 3 |
| G38004 | High | High | 2 | 2 |
| G38007 | High | Moderate | 1 | 3 |
| G38008 | Moderate | Moderate | 1 | 3 |
| G38010 | High | High | 2 | 2 |
| G38012 | High | Moderate | 3 | 3 |
| G38015 | High | High | 4 | 3 |
| G38018 | Moderate | High | 3 | 3 |
| G38022 | High | High | 3 | 3 |
| G38028 | Moderate | High | 3 | 3 |
| G38029 | High | High | 3 | 3 |
| Fireball | 0 | High | 3 | 3 |

2) Gp2 Protein Activity from Transgenic Plants

To test if the Gp2 protein expressed in transgenic plants was active, leaf IF extractions from a set of moderate to very high expressing transformants were used in the in vitro antibiosis assay described in Example 19 (microtiter plate assay). *Fusarium oxysporum* fsp. *lycopersici* Race 1 was used as the test pathogen. Evaluations were made with leaf IF protein extracts at a concentration of ~10 µg protein/100 µl growth medium. One-half strength Potato Dextrose Broth supplemented with 2.5 mM $NaCl_2$ and 50 mM KC1 was used as the growth medium. The initial fungal evaluation was adjusted to approximately $1\times10^3$ spores/100 $\mu$l. Fungal growth was monitored over 2 to 3 days. Each treatment was replicated 3 times and some treatments were repeated. Optical density values followed by an asterisk were significantly different than the control (comparisons were made to either IF extracts from Fireball or 92550). Only plants which exhibited moderate to high levels of Gp2 expression were screened. Analysis of variance was used to analyze the data and the Duncan's test was used from mean comparisons. To measure the interaction of effects of different treatments over time, orthogonal contrasts were used.

Four plants out of the eleven screened showed a statistically significant reduction in mycelial growth during the first 24 hours as compared to the control (Table 12). For some lines, duplicate readings were taken as shown. Three other lines showed a reduction in growth but differences were not statistically significant. The remaining four lines exhibited no inhibition. IF extracts from line F38005 exhibited the most fungal inhibition. Line F38005 also had the highest Gp2 protein and RNA levels of any transformant. The amount of inhibition observed from the transformed tomato extracts was less than that observed from pepper IF extracts.

TABLE 12

Summary ot antifungal activity assay: leaf IF extracts from selected Gp2 expressing tomato lines

| Line | Expression phenotype | % inhibition |
|---|---|---|
| F38001 | moderate | 20, 51* |
| F38005 | very high | 36*, 61* |
| G38002 | moderate | 0 |
| G38003 | high | 44*, 35 |
| G38004 | high | 0, 0 |
| G38007 | moderate | 0, 34 |
| G38010 | high | 34*, 0 |
| G38012 | moderate | 2, 0 |
| G38015 | high | 0, 0 |
| G38022 | high | 12, 0 |
| G38029 | high | 13 |

Optical density values followed by an asterisk were significantly different than the control. The control treatment was the pathogen growing in medium alone.

Example 21

Evaluation of Tomato Lines Expressing Gp2 for Disease Resistance/tolerance to Selected Fungal Pathogens A set of segregating tomato lines that had moderate to high expression of Gp2 were evaluated for disease tolerance against *Fusarium oxysporum* fsp. *lycopersici* Race 1 and *Verticillium dahliae* Race 1 in greenhouse trials. Plants were inoculated by dipping 10–12 day seedlings into a spore suspension of Fusarium at $1\times10^6$ spores/ml or Verticillium at $1\times10^6$ spores/ml for twenty minutes. Inoculated plants were then planted to potting mix, grown in the greenhouse and evaluated for disease by rating symptoms over time. A completely randomized block design was used, with 4 replications per line and 8 plants per replication. Disease severity was rated based on a scale from 1 to 5 where 1=dead plant and 5=disease symptoms. To rate the vascular system for the Verticillium infection, stems were cut longitudinally and the amount of necrosis rated as disease severity 1 to 5 where 1=severe necrosis throughout the entire vascular cylinder to 5=no disease. Data was analyzed with the ANOVA procedure of Statview™ and means comparison were made using Duncan's Multiple Range Test (P=0.05). In Table 13, treatments with similar letters are not significantly different from each other (nd=not determined).

Lines F38005, G38022, G38015, G38018, G38012, G38028 and G38029 were tested and repeated, and comparable results were obtained. Fireball, F92550, and VFN8 were controls. In the Verticillium experiment, all lines in the Fireball background exhibited some degree of tolerance against infection and had higher survival than the control (Fireball) (Table 13). This was true for disease severity ratings for both wilt and necrosis in the vascular cylinder. Examination of the vascular cylinder of the transformed lines showed that the disease did not progress as far into the top of the shoot as disease in the Fireball control. Lines G38012 and G38022 were significantly less susceptible to Verticillium or Fusarium than the control (Fireball). Lines G38018 and G38028 exhibited less infection against Fusarium at week 3 compared to controls, but by week 4 they were infected at levels similar to the control plants. Both lines displayed statistically significantly less disease than the controls when infected by Verticillium.

Line F38005 was also highly resistant against Verticillium, but this effect is due to natural resistance since its parent line, F92550, showed a similar phenotype.

TABLE 13

Evaluation of transgenic tomato lines expressing Gp2 protein for disease tolerance against Fusarium wilt Race 1 and Verticillium wilt Race 1

| | | Disease severity | | | | |
| --- | --- | --- | --- | --- | --- | --- |
| | | Fusarium | | Verticillium | | Vascular |
| Lines | Loci | Week 3 | Week 4 | Week 3 | Week 4 | necrosis |
| Fireball | op | 2.5a | 1.1a | 2.4a | 1.4a | 2.4a |
| G38028 | nd | 3.2b | 1.9ab | 2.4a | 1.7b | 3.0b |
| G38018 | 1 | 3.1b | 1.9ab | 2.6abc | 1.7b | 3.4b |
| G38022 | 1 | 4.1c | 2.2b | 2.7c | 2.0cd | 3.3b |
| G38012 | 1 | 3.5b | 2.3b | 2.7c | 2.2cd | 3.3b |
| G38015 | 2 | 2.6a | 1.5ab | 4.4d | 4.4ef | 4.5cd |
| G38029 | 1 | 2.3a | 1.6ab | 2.7c | 2.1d | 3.4b |
| F92550 | op | 2.4a | 1.7b | 4.4d | 4.5g | 4.5cd |
| F38005 | 1 | 2.3a | 1.5b | 4.4d | 4.4g | 4.3c |
| VFN8 | F1 | 5c | 4.5d | 4.8c | 4.5g | 4.8d |

Disease rating: 1 = dead plant to 5 = no disease symptoms
Means comparison were made using Duncan's Multiple Range Test (P = 0.5)

Inoculum levels: Fusarium at $1 \times 10^5$ spores/ml and Verticillium at $1 \times 10^6$ spores/ml The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated polynucleotide comprising a first nucleic acid sequence encoding an antimicrobial protein, wherein the first nucleic acid sequence hybridizes under stringent conditions to a second nucleic acid sequence encoding a protein having the amino acid sequence depicted in SEQ ID NO:2.

2. The isolated polynucleotide of claim 1, wherein the first nucleic acid sequence hybridizes under stringent conditions to a second nucleic acid sequence having the nucleic acid sequence depicted in SEQ ID NO:1.

3. The isolated polynucleotide of claim 1, wherein the first nucleic acid sequence hybridizes under stringent conditions to a second nucleic acid sequence having the nucleic acid sequence depicted in SEQ ID NO:3.

4. The isolated polynucleotide of claim 1, wherein the first nucleic acid sequence has the nucleic acid sequence depicted in SEQ ID NO:1.

5. The isolated polynucleotide of claim 1, wherein the first nucleic acid sequence encodes an antimicrobial protein having the amino acid sequence depicted in SEQ ID NO:2.

6. The isolated polynucleotide of claim 1, wherein the first nucleic acid sequence is operably linked to a plant promoter.

7. The isolated polynucleotide of claim 6, wherein the first nucleic acid sequence is operably linked to a heterologous plant promoter.

8. The isolated polynucleotide of claim 6, wherein the first nucleic acid sequence is operably linked to a plant Gp2 promoter which is capable of initiating constitutive transcription in a Solanaceous plant cell, wherein the promoter has between about 250 and about 1250 nucleotides and hybridizes to a nucleic acid having a sequence as shown in SEQ ID NO. 4 under hybridization conditions which include washing at 65 C. in 0.1×SSC, 0.1% SDS.

9. The isolated polynucleotide of claim 7, wherein the first nucleic acid sequence is operably linked to a heterologous plant promoter capable of constitutive expression in a plant cell.

10. The isolated polynucleotide of claim 1, wherein the first nucleic acid is from a member of the family Solanaceae.

11. The isolated polynucleotide of claim 1, wherein the first nucleic acid is from a pepper plant.

12. A recombinant expression cassette comprising a first nucleic acid sequence encoding an antimicrobial protein operably linked to a plant promoter, wherein the first nucleic acid sequence hybridizes under stringent conditions to a second nucleic acid sequence encoding an antimicrobial protein having the amino acid depicted in SEQ ID NO:2.

13. A recombinant expression cassette of claim 12, wherein the promoter is a heterologous plant promoter.

14. A recombinant expression cassette of claim 12, wherein the promoter is a plant Gp2 promoter.

15. A transgenic plant comprising recombinant polynucleotide comprising a first nucleic acid sequence encoding an antimicrobial protein, wherein the first nucleic acid sequence hybridizes under stringent conditions to a second nucleic acid sequence encoding a plant protein having the amino acid depicted in SEQ ID NO:2.

16. The transgenic plant of claim 15, wherein the first nucleic acid sequence hybridizes under stringent conditions to a second nucleic acid sequence having the nucleic acid sequence depicted in SEQ ID NO:1.

17. The transgenic plant of claim 15, wherein the first nucleic acid sequence has the nucleic acid sequence depicted in SEQ ID NO:1.

18. The transgenic plant of claim 15, wherein the first nucleic acid sequence encodes an antimicrobial protein having the amino acid sequence depicted in SEQ ID NO:2.

19. The transgenic plant of claim 17, wherein the first nucleic acid sequence is operably linked to a plant promoter.

20. The transgenic plant of claim 19, wherein the first nucleic acid sequence is operably linked to a heterologous plant promoter.

21. The transgenic plant of claim 19, wherein the first nucleic acid sequence is operably linked to a plant Gp2 promoter which is capable of initiating constitutive transcription in a Solanaceous plant cell, wherein the promoter has between about 250 and about 1250 nucleotides and hybridizes to a nucleic acid having a sequence as shown in SEQ ID NO. 4 under hybridization conditions which include washing at 65 C. in 0.1×SSC, 0.1% SDS.

22. The transgenic plant of claim 20, wherein the first nucleic acid sequence is operably linked to a heterologous plant promoter capable of constitutive expression in a plant cell.

23. The transgenic plant of claim 15, wherein the first nucleic acid sequence is from a member of the family Solanaceae.

24. The transgenic plant of claim 15, wherein the first nucleic acid sequence is from a pepper plant.

25. The transgenic plant of claim 15, wherein the transgenic plant is selected from the group consisting of a pepper plant and a tomato plant.

26. The isolated polynucleotide of claim 8, wherein the plant promoter is SEQ ID NO:4.

27. The isolated polynucleotide of claim 21, wherein the plant promoter is SEQ ID NO:4.

* * * * *